(12) United States Patent
Jang et al.

(10) Patent No.: US 11,499,173 B2
(45) Date of Patent: Nov. 15, 2022

(54) MODIFIED POLYPEPTIDE WITH ATTENUATED ACTIVITY OF CITRATE SYNTHASE AND METHOD FOR PRODUCING L-AMINO ACID USING THE SAME

(71) Applicant: CJ CHEILJEDANG CORPORATION, Seoul (KR)

(72) Inventors: Jaewon Jang, Suwon-si (KR); Kwang Woo Lee, Suwon-si (KR); Yong Uk Shin, Yongin-si (KR); Imsang Lee, Yongin-si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 67 days.

(21) Appl. No.: 16/470,030

(22) PCT Filed: Feb. 12, 2019

(86) PCT No.: PCT/KR2019/001697
§ 371 (c)(1),
(2) Date: Jun. 14, 2019

(87) PCT Pub. No.: WO2019/160301
PCT Pub. Date: Aug. 22, 2019

(65) Prior Publication Data
US 2021/0355514 A1  Nov. 18, 2021

(30) Foreign Application Priority Data
Feb. 13, 2018  (KR) ........................ 10-2018-0017400

(51) Int. Cl.
| | | |
|---|---|---|
| *C12P 13/08* | (2006.01) | |
| *C12N 1/20* | (2006.01) | |
| *C12N 9/10* | (2006.01) | |
| *C12P 13/06* | (2006.01) | |
| *C12P 13/12* | (2006.01) | |
| *C12R 1/15* | (2006.01) | |

(52) U.S. Cl.
CPC ............... *C12P 13/08* (2013.01); *C12N 1/20* (2013.01); *C12N 9/1025* (2013.01); *C12P 13/06* (2013.01); *C12P 13/12* (2013.01); *C12R 2001/15* (2021.05); *C12Y 203/03001* (2013.01)

(58) Field of Classification Search
None
See application file for complete search history.

(56) References Cited

U.S. PATENT DOCUMENTS

2007/0122887 A1* 5/2007 Klopprogge ........... C07K 14/34
 435/106
2009/0280542 A1* 11/2009 Bathe ........................ C12N 9/88
 435/115

2010/0261257 A1 10/2010 Bathe et al.
2012/0214211 A1  8/2012 Bathe et al.
2016/0355830 A1 12/2016 Moon et al.

FOREIGN PATENT DOCUMENTS

| EP | 2 998 338 A1 | 3/2016 |
|---|---|---|
| KR | 10-0073610 B1 | 2/1994 |
| KR | 2009-0094433 A | 9/2009 |
| KR | 10-0924065 B1 | 10/2009 |
| KR | 10-1641770 A | 7/2016 |

OTHER PUBLICATIONS

Accession P42457. Nov. 1, 1995 (Year: 1995).*
Li et al. Biotechnol Bioeng. Jul. 2014;111(7):1273-87. Epub May 6, 2014. (Year: 2014).*
Chica et al. Curr Opin Biotechnol. Aug. 2005;16(4):378-84. (Year: 2005).*
Singh et al. Curr Protein Pept Sci. 2017, 18, 1-11 (Year: 2017).*
Eikmanns et al., Nucleotide sequence, expression and transcriptional analysis of the *Corynebacterium glutamicum gltA* gene encoding citrate synthase, *Microbiology* 140:1817-1828 (1994).
Baumgart et al., "Deletion of the Aconitase Gene in *Corynebacterium glutamicum* Causes Strong Selection Pressure for Secondary Mutations Inactivating Citrate Synthase," *Journal of Bacteriology* 193(24):6864-6873 (Dec. 2011).
Binder et al., "A high-throughput approach to identify genomic variants of bacterial metabolite producers at the single-cell level," *Genome Biology* 13:R340 (12 pages) (2012).
Morbach et al., "$_L$-Isoleucine Production with *Corynebacterium glutamicum*: Further Flux Increase and Limitation of Export," *Applied and Environmental Microbiology* 62(12):4345-4351 (Dec. 1996).
Morbach et al., "Engineering the homoserine dehydrogenase and threonine dehydratase control points to analyse flux toward $_L$-isoleucine in *Corynebacterium glutamicum*," *Appl Microbiol Biotechnol* 45:612-620 (1996).
Van Der Rest et al., "A heat shock following electroporation induces highly efficient transformation of *Corynebacterium glutamicum* with xenogeneic plasmic DNA," *Appl Microbiol Biotechnol* 52:541-545 (1999).
Van Ooyen et al., "Improved $_L$-Lysine Production With *Corynebacterium glutamicum* and Systemic Insight into Citrate Synthase Flux and Activity," *Biotechnology and Bioengineering* (12 pages) (2012).
Zhou et al., "Exploring Lysine Riboswitch for Metabolic Flux Control and Improvement of $_L$-Lysine Synthesis in *Corynebacterium glutamicum*," *ACS Synth. Biol.* (six pages) (Aug. 3, 2014).

\* cited by examiner

*Primary Examiner* — Christian L Fronda
(74) *Attorney, Agent, or Firm* — Seed IP Law Group LLP

(57) ABSTRACT

The present disclosure relates to a modified polypeptide with attenuated activity of citrate synthase and a method for producing an aspartate-derived L-amino acid using the modified polypeptide.

9 Claims, 1 Drawing Sheet
Specification includes a Sequence Listing.

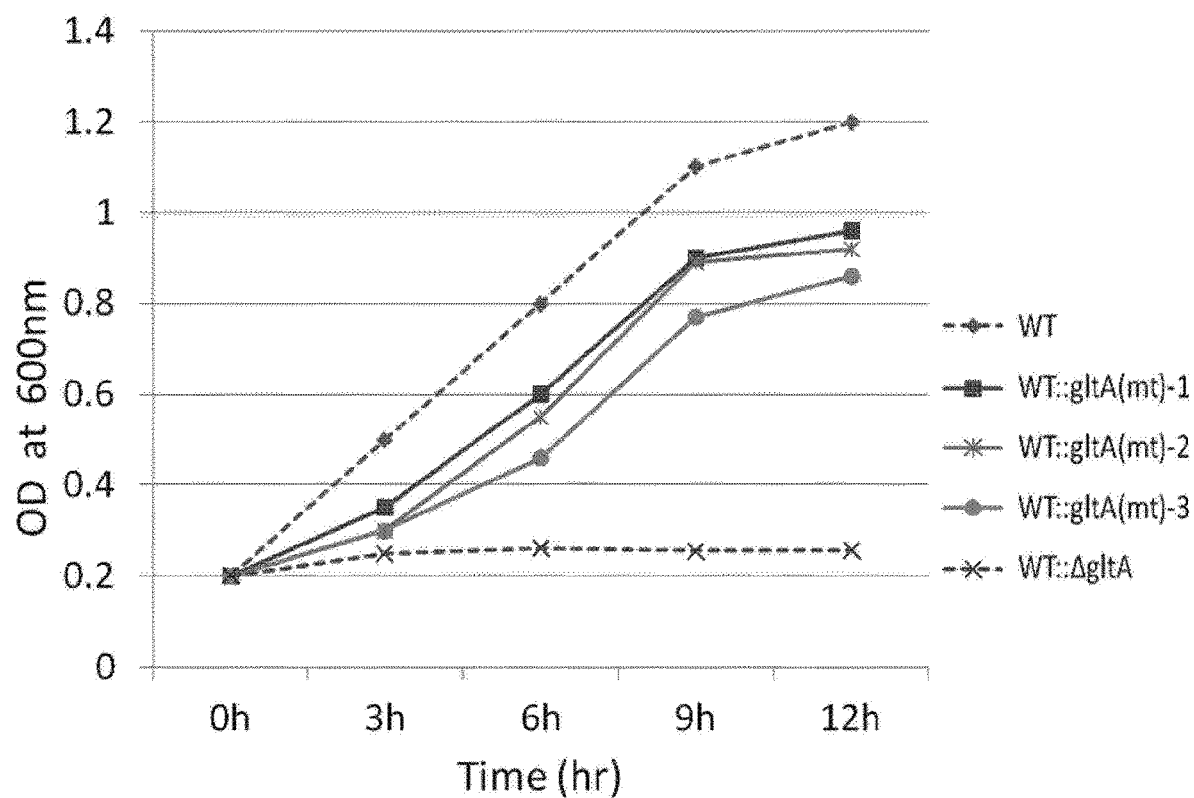

MODIFIED POLYPEPTIDE WITH ATTENUATED ACTIVITY OF CITRATE SYNTHASE AND METHOD FOR PRODUCING L-AMINO ACID USING THE SAME

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200187_444_USPC_SEQUENCE_LISTING.txt. The text file is 30 KB, was created on May 16, 2019, and is being submitted electronically via EFS-Web.

TECHNICAL FIELD

The present disclosure relates to a modified polypeptide with attenuated activity of citrate synthase and a method for producing L-amino acid using the modified polypeptide.

BACKGROUND ART

A microorganism of the genus *Corynebacterium*, specifically *Corynebacterium glutamicum*, is a Gram-positive microorganism that is widely used in the production of L-amino acid and other useful materials. For the production of the L-amino acid and other useful materials, various studies are underway to develop microorganisms with high-efficiency production and technologies for fermentation processes. For example, target material specific approaches (e.g., increasing the expression of genes encoding the enzymes involved in L-lysine biosynthesis or removing genes unnecessary for biosynthesis) are mainly used (KR Patent No. 10-0838038).

Meanwhile, among L-amino acids, L-lysine, L-threonine, L-methionine, L-isoleucine, and L-glycine are aspartate-derived amino acids, and the biosynthesis level of oxaloacetate (i.e., a precursor of aspartate) can affect the biosynthesis levels of these L-amino acids.

Citrate synthase (CS) is an enzyme that produces citrate by catalyzing the condensation of acetyl-CoA and oxaloacetate produced during glycolysis of a microorganism, and it is also an important enzyme for determining carbon-flow into the TCA pathway.

The phenotypic changes in L-lysine-producing strains due to the deletion of gltA gene encoding citrate synthase were reported previously in a literature (Ooyen et al., Biotechnol. Bioeng., 109(8): 2070-2081, 2012). However, these strains with the deletion of gltA gene have disadvantages in that not only their growth is inhibited but also their sugar consumption rates are significantly reduced thus resulting in low lysine production per unit time. Accordingly, there is still a need for studies in which an effective increase in L-amino acid productivity and the growth of the strains can be both considered.

DISCLOSURE

Technical Problem

The present inventors have confirmed that when a novel modified polypeptide in which citrate synthase activity is attenuated to a certain level is used, the amount of L-amino acid production can be increased without delay in the growth rate of the strain, thereby completing the present disclosure.

Technical Solution

An object of the present disclosure is to provide a modified polypeptide with citrate synthase activity, in which the $241^{st}$ amino acid in the amino acid sequence of SEQ ID NO: 1, asparagine, is substituted with another amino acid.

Another object of the present disclosure is to provide a polynucleotide encoding the modified polypeptide.

Still another object of the present disclosure is to provide a microorganism of the genus *Corynebacterium* producing an aspartate-derived L-amino acid, comprising the modified polypeptide.

Still another object of the present disclosure is to provide a method for producing an L-amino acid, which includes culturing the microorganism of the genus *Corynebacterium* in a medium; and recovering an L-amino acid from the cultured microorganism or medium.

Advantageous Effect

When the novel modified polypeptide of the present disclosure with attenuated citrate synthase activity is used, the amount of aspartate-derived L-amino acid production can be further improved without delaying the growth rate.

BRIEF DESCRIPTION OF DRAWINGS

FIG. 1 shows the growth curve of a strain in which deletion and modification of gltA gene are introduced.

BEST MODE

The present disclosure is described in detail as follows. Meanwhile, respective descriptions and embodiments disclosed in the present disclosure may also be applied to other descriptions and embodiments. That is, all combinations of various elements disclosed in the present disclosure fall within the scope of the present disclosure. Further, the scope of the present disclosure is not limited by the specific description below.

To achieve the above objects, an aspect of the present disclosure provides a modified polypeptide having citrate synthase activity, in which the modified polypeptide includes at least one modification in the amino acid of SEQ ID NO: 1 and the at least one modification includes substitution of the $241^{st}$ amino acid in the amino acid sequence of SEQ ID NO: 1 (i.e., asparagine) with another amino acid.

Specifically, the modified polypeptide may be described as a modified polypeptide having citrate synthase activity, in which the $241^{st}$ amino acid in the amino acid sequence of SEQ ID NO: 1 (i.e., asparagine) is substituted with another amino acid.

In the present disclosure, the SEQ ID NO: 1 refers to an amino acid sequence having the activity of citrate synthase, and specifically, a protein sequence having the activity of citrate synthase encoded by gltA gene. The amino acid sequence of SEQ ID NO: 1 may be obtained from NCBI GenBank, which is a public database. For example, the amino acid sequence of SEQ ID NO: 1 may be derived from *Corynebacterium glutamicum*, but the amino acid sequence is not limited thereto, and may include any sequence having the same activity as that of the above amino acid sequence without limitation. Further, the amino acid sequence may include the amino acid sequence of SEQ ID NO: 1 or any amino acid sequence having 80% or more homology or identity to the amino acid sequence of SEQ ID NO: 1, but the amino acid sequence is not limited thereto. Specifically, the amino acid sequence may include the amino acid sequence of SEQ ID NO: 1 and any amino acid sequence having at least 80%, 90%, 95%, 96%, 97%, 98%, or 99% or more homology to the amino acid sequence of SEQ ID NO: 1. Further, it is apparent that any protein having an amino acid sequence, in which part of the amino acid sequence is deleted, modified, substituted, or added, may also be used in the present disclosure as long as the protein has such a homology or identity in an amino acid sequence to that of the above protein and exhibits an effect corresponding to that of the above protein.

That is, in the present disclosure, although it is described as "protein or polypeptide having an amino acid sequence of a particular SEQ ID NO" or "protein or polypeptide consisting of an amino acid sequence of a particular SEQ ID NO", it is apparent that any protein which has biological activity substantially the same as or equivalent to the polypeptide consisting of the amino acid sequence of the corresponding SEQ ID NO may be used in the present disclosure, even if the amino acid sequence may have deletion, modification, substitution, or addition in part of the sequence. For example, it is apparent that the "polypeptide consisting of an amino acid sequence of SEQ ID NO: 1" can belong to the "polypeptide consisting of an amino acid sequence of SEQ ID NO: 1". Additionally, in a case where the polypeptide has activity the same as or equivalent to the modified polypeptide of the present disclosure, a mutation that can occur due to a meaningless sequence addition upstream or downstream of the amino acid sequence of the corresponding SEQ ID NO, a naturally occurring mutation, or a silent mutation therein is not excluded, in addition to a modification on the $241^{st}$ amino acid or a modification corresponding thereto, and it is apparent that in cases where the polypeptide has such a sequence addition or mutation, the resulting peptides can also belong to the scope of the present disclosure.

As used herein, the term "homology" or "identity" represents relevance between two given amino acid sequences or nucleotide sequences and may be expressed as percentage. These two terms "homology" and "identity" are often used interchangeably with each other.

The sequence homology or identity of conserved polynucleotide or polypeptide sequences may be determined by standard alignment algorithms and may be used with default gap penalty established by the program being used. Substantially homologous or identical sequences are generally expected to hybridize under moderate or high stringent conditions, along the entire length or at least about 50%, about 60%, about 70%, about 80%, or about 90% of the entire length of the target polynucleotides or polypeptides. With respect to the hybridization, polynucleotides that contain degenerate codons instead of the codons in the hybridizing polypeptides are also considered.

Whether any two polynucleotide or polypeptide sequences have a homology or identity may be determined using a known computer algorithm, such as the "FASTA" program using default parameters as described by Pearson et al. (*Proc. Natl. Acad. Sci. USA* 85: 2444, (1988)). Alternatively, the homology or identity may be determined using the Needleman-Wunsch algorithm (Needleman and Wunsch, 1970, *J Mol. Biol.* 48: 443-453), which is performed in the Needleman program of the EMBOSS package (EMBOSS: The European Molecular Biology Open Software Suite, Rice et al., 2000, *Trends Genet.* 16: 276-277) (preferably, version 5.0.0 or versions thereafter) (GCG program package (Devereux, J., et al., *Nucleic Acids Research* 12: 387 (1984)), BLASTP, BLASTN, FASTA (Atschul, [S.] [F.,] et al., *J Molec* Bio 215]: 403 (1990); Guide to Huge Computers, Martin J. Bishop, [ED.], Academic Press, San Diego, 1994, and [CARILLO ETA/.](1988) SIAM *J Applied Math* 48: 1073). For example, the homology, similarity, or identity may be determined using BLAST or ClustalW of the National Center for Biotechnology Information.

The homology, similarity, or identity between polynucleotides or polypeptides may be determined by comparing sequence information using, for example, the GAP computer program (e.g., Needleman et al. (1970), *J Mol. Biol.* 48: 443) as disclosed in the literature (Smith and Waterman, *Adv. Appl. Math* (1981) 2:482). In summary, the GAP program defines homology, similarity, or identity as the value obtained by dividing the number of similarly aligned symbols (i.e., nucleotides or amino acids) by the total number of the symbols in the shorter of the two sequences. Default parameters for the GAP program may include (1) a unary comparison matrix (containing a value of 1 for identities and 0 for non-identities) and the weighted comparison matrix of Gribskov et al. (1986), *Nucl. Acids Res.* 14: 6745, as disclosed in the literature (Schwartz and Dayhoff, eds., *Atlas of Protein Sequence and Structure*, National Biomedical Research Foundation, pp. 353-358, 1979); (2) a penalty of 3.0 for each gap and an additional 0.10 penalty for each symbol in each gap (or a gap opening penalty of 10 and a gap extension penalty of 0.5); and (3) no penalty for end gaps.

Additionally, whether any two polynucleotide or polypeptide sequences have a homology, similarity, or identity may be determined by comparing these sequences via Southern hybridization experiments, and the appropriate hybridization conditions to be defined may be determined by a method known to those skilled in the art (e.g., J. Sambrook et al., *Molecular Cloning, A Laboratory Manual, 2nd Edition*, Cold Spring Harbor Laboratory press, Cold Spring Harbor, N.Y., 1989; F. M. Ausubel et al., *Current Protocols in Molecular Biology*, John Wiley & Sons, Inc., New York).

As used herein, the term "modified polypeptide" refers to a polypeptide, in which one or more amino acids differ from those of the recited sequence in conservative substitution and/or modification, but the functions or properties of the polypeptide are maintained. The modified polypeptide differs from those sequences which are identified by substitution, deletion, or addition of several amino acids. Such a modified polypeptide can generally be identified by modifying one of the polypeptide sequences and evaluating the properties of the modified polypeptide. That is, the ability of a modified polypeptide may be increased, unchanged, or decreased relative to that of the native protein. Such a modified polypeptide can generally be identified by modifying one of the polypeptide sequences and evaluating the reactivity of the modified polypeptide. Additionally, a partially modified polypeptide may include a modified polypeptide in which one or more parts therein (e.g., a N-terminal leader sequence, a transmembrane domain, etc.) are removed. Other modified polypeptides may include those polypeptides in which a part therein is removed from the N- and/or C-terminus of each mature protein. In the present disclosure, the term "modified" may be used interchangeably with terms, such as modification, modified protein, modified polypeptide, mutant, mutein, divergent, variant, etc., and the term is not limited as long as it is used as a meaning of modification.

As used herein, the term "conservative substitution" refers to substitution of an amino acid with another amino acid having similar structural and/or chemical properties.

The variant (modified polypeptide) may have, for example, one or more conservative substitutions while maintaining one or more biological activities. This amino acid substitution may be generally performed based on similarity in polarity, electric charge, solubility, hydrophobicity, hydrophilicity, and/or amphipathic nature of amino acid residues. For example, among the electrically charged amino acids, positively charged (basic) amino acids include arginine, lysine, and histidine; and negatively charged (acidic) amino acids include glutamic acid and aspartic acid; and among the uncharged amino acids, nonpolar amino acids include glycine, alanine, valine, leucine, isoleucine, methionine, phenylalanine, tryptophan, and proline; polar or hydrophilic amino acids include serine, threonine, cysteine, tyrosine, asparagine, and glutamine; and among the polar amino acids, aromatic amino acids include phenylalanine, tryptophan, and tyrosine.

In addition, variants (modified polypeptide) may include deletion or addition of amino acids having a minimal effect on the characteristics and secondary structure of a polypeptide. For example, a polypeptide may be conjugated to a signal (or leader) sequence of a protein N-terminus that is involved in the transfer of proteins co-translationally or post-translationally. Additionally, the polypeptide may also be conjugated to another sequence or linker to be identified, purified, or synthesized.

The modified polypeptide of the present disclosure may be a modified polypeptide with attenuated citrate synthase activity compared to that of the amino acid sequence of SEQ ID NO: 1, in which the modified polypeptide includes at least one modification in the amino acid of SEQ ID NO: 1, and the at least one modification includes substitution of the $241^{st}$ amino acid in the amino acid sequence of SEQ ID NO: 1 (i.e., asparagine) with another amino acid. The modified polypeptide may be described as a modified polypeptide with attenuated citrate synthase activity compared to that of the amino acid sequence of SEQ ID NO: 1, in which the $241^{st}$ amino acid in the amino acid sequence of SEQ ID NO: 1 is substituted with another amino acid.

The "substitution with another amino acid" is not limited as long as the amino acid substituted differs from the amino acid before substitution. That is, when the $241^{st}$ amino acid in the amino acid sequence of SEQ ID NO: 1 substituted with another amino acid, the another amino acid is not limited as long as the another amino acid is an amino acid other than asparagine.

The modified polypeptide of the present disclosure may be one which has reduced or attenuated activity of citrate synthase compared to the polypeptide before modification, native wild-type polypeptide, or unmodified polypeptide, but the modified polypeptide is not limited thereto.

Specifically, the modified polypeptide of the present disclosure may be one, in which the $241^{st}$ amino acid in the amino acid sequence of SEQ ID NO: 1 (i.e., asparagine) is substituted with glycine, alanine, arginine, aspartate, cysteine, glutamate, glutamine, histidine, proline, serine, tyrosine, isoleucine, leucine, lysine, tryptophan, valine, methionine, phenylalanine, or threonine. More specifically, the modified polypeptide may be one, in which the $241^{st}$ amino acid in the amino acid sequence of SEQ ID NO: 1 (i.e., asparagine) is substituted with an amino acid other than lysine, but the substitution is not limited thereto. Alternatively, the modified polypeptide may be one, in which the $241^{st}$ amino acid in the amino acid sequence of SEQ ID NO: 1 (i.e., asparagine) is substituted with an amino acid other than an acidic or basic amino acid, or substituted with an amino acid having an uncharged amino acid, but the substitution is not limited thereto. Alternatively, the modified polypeptide may be one, in which the $241^{st}$ amino acid in the amino acid sequence of SEQ ID NO: 1 (i.e., asparagine) is substituted with a nonpolar amino acid or hydrophilic amino acid, and specifically with an aromatic amino acid (e.g., phenylalanine, tryptophan, and tyrosine) or a hydrophilic amino acid (e.g., serine, threonine, tyrosine, cysteine, asparagine, and glutamine), but the modified polypeptide is not limited thereto. More specifically, the modified polypeptide may be one with attenuated citrate synthase activity, in which the $241^{st}$ amino acid in the amino acid sequence of SEQ ID NO: 1 (i.e., asparagine) is substituted with threonine, serine, or tyrosine, but the modified polypeptide is not limited thereto. Even more specifically, the modified polypeptide may be one with attenuated citrate synthase activity, in which the $241^{st}$ amino acid in the amino acid sequence of SEQ ID NO: 1 (i.e., asparagine) is substituted with threonine, but the modified polypeptide is not limited thereto.

Such a modified polypeptide has citrate synthase activity which is attenuated compared to that of the polypeptide having the amino acid sequence of SEQ ID NO: 1. It is apparent that the modified polypeptide, in which the $241^{st}$ amino acid in the amino acid sequence of SEQ ID NO: 1 is substituted with another amino acid, includes modified polypeptides in which any amino acid corresponding to the $241^{st}$ amino acid is substituted with another amino acid.

Specifically, among the modified polypeptides, the modified polypeptide in which the $241^{st}$ amino acid in the amino acid sequence of SEQ ID NO: 1 (i.e., asparagine) is substituted with another amino acid may be one which consists of SEQ ID NOS: 3, 59, and 61, and more specifically, the modified polypeptide in which the $241^{st}$ amino acid in the amino acid sequence of SEQ ID NO: 1 (i.e., asparagine) is substituted with threonine, serine, or tyrosine may be one which consists of each of SEQ ID NOS: 3, 59, and 61, but the modified polypeptide is not limited thereto. Additionally, the modified polypeptide may include the amino acid sequences of SEQ ID NOS: 3, 59, and 61, or amino acid sequences which have at least 80% of a homology to each of the amino acid sequences of SEQ ID NOS: 3, 59, and 61, but the modified polypeptide is not limited thereto. Specifically, the modified polypeptide of the present disclosure may include the amino acid sequences of SEQ ID NOS: 3, 59, and 61, or amino acid sequences which have at least 80%, at least 90%, at least 95%, at least 96%, at least 97%, at least 98%, or at least 99% of a homology to each of the amino acid sequences of SEQ ID NOS: 3, 59, and 61. Additionally, it is apparent that any protein having an amino acid sequence with deletion, modification, substitution, or addition in part of the amino acid sequence, in addition to the $241^{st}$ amino acid of the amino acid sequence, can also be included in the scope of the present disclosure, as long as the amino acid sequence has the homology described above and has an effect corresponding to that of the protein.

As used herein, the term "citrate synthase (CS)" refers to an enzyme that produces citrate by catalyzing the condensation of acetyl-CoA and oxaloacetate produced during glycolysis of a microorganism, and it is an important enzyme that determines carbon-flow into the TCA pathway. Specifically, citrate synthase acts as a factor to regulate the rate in the first step of the TCA cycle as an enzyme for synthesizing citrate. In addition, the citrate synthase catalyzes the condensation reaction of the two-carbon acetate residue from acetyl-CoA and a molecule of 4-carbon oxaloacetate to form the 6-carbon acetate. In the present disclosure, the citrate synthase may be used interchangeably with "enzyme for synthesizing citrate" or "CS".

Another aspect of the present disclosure provides a polynucleotide encoding the modified polypeptide.

As used herein, the term "polynucleotide", which is a polymer of nucleotides composed of nucleotide monomers connected in a lengthy chain by a covalently bond, is a DNA or RNA strand having at least a certain length, and more specifically, a polynucleotide fragment encoding the modified polypeptide.

The polynucleotide encoding the modified polypeptide of the present disclosure may include without limitation any polynucleotide sequence encoding a modified polypeptide with attenuated citrate synthase activity of the present disclosure. In the present disclosure, the gene encoding the amino acid sequence of the citrate synthase polypeptide may be the gltA gene, specifically a gene derived from *Corynebacterium glutamicum*, but the gene is not limited thereto.

The polynucleotide of the present disclosure may undergo various modifications in the coding region without changing the amino acid sequence of the polynucleotide, due to codon degeneracy or in consideration of the codons preferred in an organism in which the polynucleotide is to be expressed. Specifically, any polynucleotide sequence encoding the modified polypeptide, in which the $241^{st}$ amino acid in the amino acid sequence of SEQ ID NO: 1 is substituted with another amino acid, may be included without limitation. For example, the polynucleotide of the present disclosure may be those which consist of the amino acid sequences of SEQ ID NOS: 3, 59, and 61, respectively, or polynucleotide sequences encoding polypeptides having a sequence homology to these polypeptides, but the polynucleotide is not limited thereto. More specifically, the polynucleotide of the present disclosure may one which consists of each polynucleotide sequence of SEQ ID NOS: 4, 60, and 62, but the polynucleotide of the present disclosure is not limited thereto.

Additionally, a probe that may be prepared from a known gene sequence, for example, any sequence which can hybridize with a sequence complementary to all or part of the polynucleotide sequence under stringent conditions to encode a protein having the activity of the modified polypeptide in which the $241^{st}$ amino acid in the amino acid sequence of SEQ ID NO: 1 is substituted with another amino acid, may be included without limitation.

The "stringent conditions" refers to conditions under which specific hybridization between polynucleotides is allowed. Such conditions are specifically described in the literature (e.g., J. Sambrook et al., supra). The stringent conditions may include conditions under which genes having a high homology, for example, 40% or higher homology, specifically 90% or higher homology, more specifically 95% or higher homology, much more specifically 97% or higher homology, still much more specifically 99% or higher homology are hybridized with each other and genes having a homology lower than the above homologies are not hybridized with each other, or ordinary washing conditions of Southern hybridization (i.e., washing once, specifically, twice or three times at a salt concentration and a temperature corresponding to 60° C., 1×SSC, 0.1% SDS, specifically, 60° C., 0.1×SSC, 0.1% SDS, and more specifically 68° C., 0.1×SSC, 0.1% SDS), but the stringent conditions are not limited thereto and may be appropriately adjusted by those skilled in the art.

Hybridization requires that two polynucleotides contain complementary sequences, although mismatches between bases are possible depending on the stringency of the hybridization. The term "complementary" is used to describe the relationship between nucleotide bases that can hybridize with each other. For example, with respect to DNA, adenosine is complementary to thymine and cytosine is complementary to guanine. Therefore, the present disclosure may include isolated nucleotide fragments complementary to the entire sequence as well as polynucleotide sequences substantially similar thereto.

Specifically, the polynucleotides having a homology may be detected using the hybridization conditions including a hybridization step at a $T_m$ value of 55° C. under the above-described conditions. Further, the $T_m$ value may be 60° C., 63° C., or 65° C., but the $T_m$ value is not limited thereto and may be appropriately adjusted by those skilled in the art depending on the purpose thereof.

The appropriate stringency for hybridizing polynucleotides depends on the length of the polynucleotides and the degree of complementation, and these variables are well known in the art (see Sambrook et al., supra, 9.50-9.51, 11.7-11.8).

Still another aspect of the present disclosure provides a microorganism comprising the modified polypeptide. Specifically, the present disclosure provides a microorganism of the genus *Corynebacterium* producing L-amino acid, comprising the modified polypeptide. More specifically, the present disclosure provides a microorganism of the genus *Corynebacterium* producing aspartate-derived L-amino acid, comprising the modified polypeptide. For example, the microorganism to be provided may be one which is transformed with a vector containing a polynucleotide encoding the modified polypeptide, but the microorganism is not limited thereto.

The microorganisms comprising the modified polypeptide of the present disclosure have an improved ability to produce L-amino acid compared to the microorganism comprising a wild-type polypeptide, without inhibition of growth or sugar consumption rate of the microorganism. Therefore, L-amino acid can be obtained in high yield from these microorganisms. Specifically, it may be interpreted that the microorganism comprising the modified polypeptide can establish a suitable balance between the carbon flow into the TCA pathway and the supply amount of oxaloacetate used as a precursor of the biosynthesis of L-amino acid by controlling the activity of citrate synthase, and as a result, the microorganism comprising the modified polypeptide can increase the amount of L-amino acid production, but the interpretation is not limited thereto.

As used herein, the term "L-amino acid" refers to an organic compound containing amine and carboxyl functional group, and specifically, an amino acid in α-amino acid form or a L stereoisomer form(L-form). The L-amino acid may be asparagine, glycine, alanine, arginine, aspartate, cysteine, glutamic acid, glutamine, histidine, proline, serine, tyrosine, isoleucine, leucine, lysine, tryptophan, valine, methionine, phenylalanine, or threonine. Additionally, the L-amino acid may be L-homoserine (an α-amino acid) or a derivative thereof as a precursor of L-amino acid, but the L-amino acid is not limited thereto. The L-homoserine derivative may be, for example, one selected from the group consisting of O-acetylhomoserine, O-succinylhomoserine, and O-phosphohomoserine, but the L-homoserine derivative is not limited thereto.

As used herein, the term "aspartate" refers to an α-amino acid which is used in the biosynthesis of proteins and may be used interchangeably with aspartic acid. Generally, aspartate is produced from oxaloacetate, which is a precursor of aspartate, and may be converted to L-lysine, L-methionine, L-homoserine or a derivative thereof, L-threonine, L-isoleucine, etc. in vivo.

As used herein, the term "aspartate-derived L-amino acid" refers to a material which can be biosynthesized using aspartate as a precursor, and the aspartate-derived L-amino acid is not limited as long as the L-amino acid can be produced via biosynthesis using aspartate as a precursor. The aspartate-derived L-amino acid may include not only aspartate-derived L-amino acid but also a derivative thereof. For example, the L-amino acid and derivative thereof may be L-lysine, L-threonine, L-methionine, L-glycine, homoserine or a derivative thereof (O-acetylhomoserine, O-succinylhomoserine, and O-phosphohomoserine), L-isoleucine, and/or cadaverine, but the L-amino acid and a derivative thereof are not limited thereto. Specifically, the L-amino acid and derivative thereof may be L-lysine, L-threonine, L-methionine, homoserine or a derivative thereof, and/or L-isoleucine, and more specifically, the L-amino acid and derivative thereof may be L-lysine, L-threonine and/or L-isoleucine, but the L-amino acid and derivative thereof are not limited thereto.

As used herein, the term "vector" refers to a DNA product including a nucleotide sequence of a polynucleotide encoding a target protein, which is operably linked to a suitable control sequence to express the target protein in a suitable host. The control sequence includes a promoter capable of initiating transcription, an arbitrary operator sequence for controlling transcription, a sequence encoding an appropriate mRNA ribosome-binding site, and sequences for controlling the termination of transcription and translation. Once transformed into a suitable host cell, the vector may replicate or function independently of the host genome or may be integrated into the genome itself.

The vector used in the present disclosure is not particularly limited as long as it can replicate in a host cell, and any vector known in the art may be used. Examples of the vector conventionally used may include natural or recombinant plasmids, cosmids, viruses, and bacteriophages. For example, as a phage vector or cosmid vector, pWE15, M13, MBL3, MBL4, IXII, ASHII, APII, t10, t11, Charon4A, Charon21A, etc., may be used; and as a plasmid vector, those based on pBR, pUC, pBluescriptII, pGEM, pTZ, pCL, pET, etc., may be used. Specifically, pDZ, pACYC177, pACYC184, pCL, pECCG117, pUC19, pBR322, pMW118, pCC1BAC vectors, etc., may be used.

The vector that can be used in the present disclosure is not particularly limited, and any known expression vector may be used. In addition, a polynucleotide encoding a target protein may be inserted into the chromosome using a vector for intracellular chromosomal insertion. The insertion of the polynucleotide into the chromosome may be performed by any method known in the art (e.g., homologous recombination), but the method is not limited thereto. The vector may further include a selection marker to confirm a successful gene insertion into the chromosome. The selection marker is for screening the cells transformed with the vector, that is, for determining whether the target polynucleotide molecule has been inserted. Markers that provide selectable phenotypes (e.g., drug resistance, auxotrophy, resistance to cell toxic agents, or expression of surface proteins) may be used. Under the circumstances treated with a selective agent, only the cells expressing the selection marker can survive or express other phenotypic traits, and thus the transformed cells can be selected.

As used herein, the term "transformation" refers to the introduction of a vector including a polynucleotide encoding a target protein into a host cell so that the protein encoded by the polynucleotide can be expressed in a host cell. As long as the transformed polynucleotide can be expressed in the host cell, it does not matter whether the transformed polynucleotide is integrated into the chromosome the host cell and located therein or located extrachromosomally. Further, the polynucleotide includes DNA and RNA encoding the target protein. The polynucleotide may be introduced in any form, as long as it can be introduced into the host cell and expressed therein. For example, the polynucleotide may be introduced into the host cell in the form of an expression cassette, which is a gene construct including all elements required for its autonomous expression. The expression cassette may include a promoter operably linked to the polynucleotide, a transcription terminator, a ribosome binding site, or a translation terminator. The expression cassette may be in the form of a self-replicable expression vector. In addition, the polynucleotide may be introduced into the host cell as it is and operably linked to sequences required for expression in the host cell, but the introduction of the polynucleotide into the cell is not limited thereto. The transformation method includes any method of introducing a polynucleotide into a cell, and may be performed by selecting a suitable standard technique known in the art, depending on the host cell. For example, the method may include electroporation, calcium phosphate ($Ca(H_2PO_4)_2$, $CaHPO_4$, or $Ca_3(PO_4)_2$) precipitation, calcium chloride ($CaCl_2$) precipitation, microinjection, a polyethyleneglycol (PEG) method, a DEAE-dextran method, a cationic liposome method, a lithium acetate-DMSO method, etc., but the method is not limited thereto.

Additionally, as used herein, the term "operable linkage" means that the polynucleotide sequence is functionally linked to a promoter sequence that initiates and mediates transcription of the polynucleotide encoding the target protein of the present disclosure. The operable linkage may be prepared using a gene recombinant technique known in the art, and site-specific DNA cleavage and linkage may be prepared using enzymes for cleavage and ligation known in the art, etc., but the preparation of the operable linkage is not limited thereto.

As used herein, the term "microorganism comprising a modified polypeptide" refers to a host cell or microorganism which includes a polynucleotide encoding a modified polypeptide, or a host cell or microorganism which is transformed with a vector including a polynucleotide encoding a modified polypeptide and is thus able to express the modified polypeptide therein. The host cell or microorganism may be of native wild-type or one in which natural or artificial genetic modification has occurred. Specifically, the microorganism of the present disclosure may be one having citrate synthase activity, in which the $241^{st}$ amino acid, asparagine, is substituted with another amino acid, thus expressing a modified polypeptide, but the microorganism is not limited thereto. Additionally, the microorganism including a modified polypeptide may be a microorganism that produces an L-amino acid. Specifically, the microorganism comprising a modified polypeptide may be a microorganism with an improved ability of L-amino acid production compared to its native type or unmodified parent strain, but the microorganism is not limited thereto. Additionally, the microorganism comprising a modified polypeptide may be a microorganism that produces an aspartate-derived L-amino acid. Specifically, the microorganism including a modified polypeptide may be a microorganism with an improved ability of aspartate-derived L-amino acid production compared to its native type or unmodified parent strain, but the microorganism is not limited thereto.

Examples of the microorganism may include a microorganism strain of the genus *Escherichia, Serratia, Erwinia,*

Enterobacteria, Salmonella, Streptomyces, Pseudomonas, Brevibacterium, Corynebacterium, etc., and specifically a microorganism of the genus Corynebacterium.

For example, the microorganism of the genus Corynebacterium may be Corynebacterium glutamicum, Corynebacterium ammoniagenes, Brevibacterium lactofermentum, Brevibacterium flavum, Corynebacterium thermoaminogenes, Corynebacterium efficiens, etc., but the microorganism of the genus Corynebacterium is not necessarily limited thereto. More specifically, the microorganism of the genus Corynebacterium may be Corynebacterium glutamicum, but the microorganism is not limited thereto.

In a specific embodiment, the microorganism may be a microorganism that produces L-lysine, in which the modification of gltA is introduced into a microorganism of the genus Corynebacterium where the activities of the proteins encoded by three kinds of modified pyc, hom, and lysC genes are increased and thereby the ability to produce L-lysine is increased.

Additionally, the microorganism may be a microorganism that produces L-threonine and L-isoleucine, in which a modification is introduced into a gene encoding homoserine dehydrogenase that produces homoserine (i.e., a common intermediate in the biosynthesis pathways for L-threonine and L-isoleucine) thereby enhancing the activity of the gene, but the microorganism is not limited thereto. In particular, the microorganism may be a microorganism that produces L-isoleucine, in which a further modification is introduced into a gene encoding L-threonine dehydratase thereby enhancing the activity of the gene, but the microorganism is not limited thereto. Accordingly, for the purpose of the present disclosure, the microorganism that produces an L-amino acid may be a microorganism in which the modified polypeptide is further added and thereby the ability of producing the target L-amino acid is increased.

Another aspect of the present disclosure provides a method for producing an L-amino acid, which includes culturing the microorganism in a medium; and recovering an L-amino acid from the cultured microorganism or medium. Specifically, the L-amino acid may be an aspartate-derived L-amino acid.

The method may be easily determined by those skilled in the art under the optimized culture conditions and enzyme activity conditions. Specifically, the microorganism may be cultured by a known batch culture, continuous culture, fed-batch culture, etc., but the culture method is not particularly limited thereto. In particular, the culture conditions are not particularly limited, but the pH (e.g., pH 5 to pH 9, specifically pH 6 to pH 8, and most specifically pH 6.8) may be appropriately adjusted using a basic compound (e.g., sodium hydroxide, potassium hydroxide, or ammonia) or an acidic compound (e.g., phosphoric acid or sulfuric acid). An aerobic condition may be maintained by adding oxygen or an oxygen-containing gas mixture to the culture. The culture temperature may be maintained at 20° C. to 45° C., and specifically at 25° C. to 40° C., and the cultivation may be performed for about 10 to 160 hours, but the culture conditions not limited thereto. The L-amino acid produced by the cultivation may be secreted into the medium or may remain within the cells.

Additionally, in the culture medium, carbon sources, such as sugars and carbohydrates (e.g., glucose, sucrose, lactose, fructose, maltose, molasses, starch, and cellulose), oils and fats (e.g., soybean oil, sunflower seed oil, peanut oil, and coconut oil), fatty acids (e.g., palmitic acid, stearic acid, and linoleic acid), alcohols (e.g., glycerol and ethanol), and organic acids (e.g., acetic acid), may be used alone or in combination, but the carbon sources are not limited thereto; nitrogen sources, such as nitrogen-containing organic compounds (e.g., peptone, yeast extract, meat juice, malt extract, corn steep liquor, soybean flour, and urea), or inorganic compounds (e.g., ammonium sulfate, ammonium chloride, ammonium phosphate, ammonium carbonate, and ammonium nitrate), may be used alone or in combination, but the nitrogen sources are not limited thereto; and potassium sources, such as potassium dihydrogen phosphate, dipotassium hydrogen phosphate, or sodium-containing salts corresponding thereto, may be used alone or in combination, but the potassium sources are not limited thereto. Additionally, other essential growth-stimulating materials including metal salts (e.g., magnesium sulfate or iron sulfate), amino acids, and vitamins may be contained in the medium.

In the method of recovering the L-amino acid produced in the cultivation step of the present disclosure, it is possible to collect the target amino acid from the culture using an appropriate method known in the art according to the cultivation method. For example, centrifugation, filtration, anion exchange chromatography, crystallization, HPLC, etc. may be used, and the desired L-amino acid may be recovered from the medium or microorganism using an appropriate method known in the art.

Further, the recovering step may include a purification process. The purification process may be performed using an appropriate method known in the art. Therefore, the L-amino acid being recovered may be in a purified form or a microorganism fermentation liquid containing the L-amino acid.

DETAILED DESCRIPTION OF THE INVENTION

Hereinafter, the present disclosure will be described in detail through exemplary embodiments. However, these exemplary embodiments are for illustrative purposes only and are not intended to limit the scope of the present disclosure.

Example 1: Preparation of Vector Library for Introducing Modification in ORF of gltA Gene For the purpose of discovering modified strains in which the expression level or activity of gltA gene of Corynebacterium glutamicum is attenuated, a library was prepared by the following method.

First, 0 to 4.5 modifications were introduced per 1 kb of a DNA fragment (1,814 bp) including the gltA gene (1,314 bp) using the GenemorphII Random Mutagenesis Kit (Stratagene). Error-prone PCR was performed using the chromosome of Corynebacterium glutamicum ATCC13032 (WT) as a template along with primers (SEQ ID NOS: 5 and 6) (Table 1). Specifically, the reaction solution containing the chromosome of the WT strain (500 ng), primers 5 and 6 (125 ng each), Mutazyme II reaction buffer (1×), dNTP mix (40 mM), and Mutazyme II DNA polymerase (2.5 U) was subjected to denaturation at 94° C. for 2 minutes followed by 25 cycles of denaturation at 94° C. for 1 minute, annealing at 56° C. for 1 minute, and polymerization at 72° C. for 3 minutes, and then polymerization at 72° C. for 10 minutes.

The amplified gene fragments were ligated to a pCRII vector using the TOPO TA Cloning Kit (Invitrogen), transformed into E. coli DH5α, and the transformed E. coli DH5a was plated on a solid LB medium containing kanamycin (25 mg/L). 20 Kinds of transformed colonies were selected and the plasmids obtained therefrom were subjected to sequence analysis. As a result, it was confirmed that modifications were introduced into sites different from each other at a frequency of 0.5 mutations/kb. Finally, about 10,000 *E. coli* transformed colonies were collected and the plasmids were extracted therefrom and named as pTOPO-gltA(mt) library.

TABLE 1

| Primer | Sequence (5'-> 3') |
| --- | --- |
| Primer (SEQ ID NO: 5) | ATGTTTGAAAGGGATATCGTG |
| Primer (SEQ ID NO: 6) | TTAGCGCTCCTCGCGAGGAAC |

Example 2: Preparation of gltA-Deleted Strains and Screening of gltA-Modified Strains Based on Growth Rate To prepare a strain of wild-type *Corynebacterium glutamicum* ATCC13032 in which the gltA gene is deleted, the pDZ-ΔgltA vector in which the gltA gene is deleted was prepared as follows. Specifically, the pDZ-ΔgltA vector (KR Patent No. 10-0924065) was prepared such that the DNA fragments (600 bp each) located at 5' and 3' of the gltA gene were ligated to the pDZ-ΔgltA vector. Primers (SEQ ID NOS: 7 and 8), in which a recognition site of the restriction enzyme (XbaI) was inserted at the 5' fragment and the 3' fragment, respectively, based on the nucleotide sequence of the reported gltA gene (SEQ ID NO: 2), and primers (SEQ ID NOS: 9 and 10), each located 600 bp apart from the primers (SEQ ID NOS: 7 and 8), were synthesized (Table 2). The 5'-end fragment was prepared by PCR using the chromosome of the *Corynebacterium glutamicum* ATCC13032 as a template along with primers (SEQ ID NOS: 7 and 9). Likewise, the gene fragment located at the 3' end of the gltA gene was prepared by PCR using the primers (SEQ ID NOS: 8 and 10). PCR was performed as follows: denaturation at 94° C. for 2 minutes; 30 cycles of denaturation at 94° C. for 1 minute, annealing at 56° C. for 1 minute, and polymerization at 72° C. for 40 seconds; and polymerization at 72° C. for 10 minutes.

Meanwhile, the DNA fragments amplified by PCR as described above were ligated to the pDZ vector, which was cleaved with a restriction enzyme (XbaI) and then heat-treated at 65° C. for 20 minutes, transformed into *E. coli* DH5α, and the transformed *E. coli* DH5a was plated on a solid LB medium containing kanamycin (25 mg/L). Colonies transformed with the vector, in which the target gene was inserted thereinto by PCR using the primers (SEQ ID NOS: 7 and 8), were selected and the plasmid was obtained from the colonies using a conventional plasmid extraction method and named as pDZ-ΔgltA.

TABLE 2

| Primer | Sequence (5'-> 3') |
| --- | --- |
| Primer (SEQ ID NO: 7) | CGGGGATCCTCTAGACGATGAAAA ACGCCC |
| Primer (SEQ ID NO: 8) | CAGGTCGACTCTAGACTGCACGTG GATCGT |

TABLE 2-continued

| Primer | Sequence (5'-> 3') |
| --- | --- |
| Primer (SEQ ID NO: 9) | ACTGGGACTATTTGTTCGGAAAAA |
| Primer (SEQ ID NO: 10) | CGAACAAATAGTCCCAGTTCAACG |

The prepared pDZ-ΔgltA vector was transformed into *Corynebacterium glutamicum* ATCC13032 by an electric pulse method (Van der Rest et al., *Appl. Microbiol. Biotechnol.* 52:541-545, 1999), and the strain in which the gltA gene is deleted was prepared by homologous recombination. The gltA gene-deleted strain was named as *Corynebacterium glutamicum* WT::ΔgltA.

Additionally, the pTOPO-gltA(mt) library was transformed by an electric pulse method using the WT::ΔgltA strain. The transformed strain was plated on a composite plate medium containing kanamycin (25 mg/L) and about 500 colonies were obtained therefrom. The obtained colonies were inoculated into a 96-well plate in which a seed culture medium (200 μL/well) was contained, and the strain was cultured at 32° C. at a rate of 1,000 rpm for about 9 hours.

<Composite Plate Medium (pH 7.0)>

Glucose (10 g), Peptone (10 g), Beef Extract (5 g), Yeast Extract (5 g), Brain Heart Infusion (18.5 g), NaCl (2.5 g), Urea (2 g), Sorbitol (91 g), Agar (20 g) (based on 1 L of distilled water)

<Seed Culture Medium (pH 7.0)>

Glucose (20 g), Peptone (10 g), Yeast Extract (5 g), Urea (1.5 g), $KH_2PO_4$ (4 g), $K_2HPO_4$ (8 g), $MgSO_4 \cdot 7H_2O$ (0.5 g), Biotin (100 μg), Thiamine.HCl (1,000 μg), Calcium-Pantothenic Acid (2,000 μg), Nicotinamide (2,000 μg) (based on 1 L of distilled water)

The cell growth during culture was monitored using the UV-spectrophotometer micro-reader (Shimazu) (FIG. 1). WT and WT::ΔgltA strains were used as control groups. Three kinds of strains, in which the cell mass was smaller but the cell growth rate was maintained at a higher rate compared to that of the wild-type (WT) strain, were selected and named as WT::gltA(mt)-1 to 3. The remaining 497 strains showed a similar or increased cell mass or a reduced growth rate compared to those of WT and WT::ΔgltA strains (control groups).

Example 3: Confirmation of Nucleotide Sequences of Three gltA-Modified Strains

To confirm the nucleotide sequences of the gltA gene of the three selected strains (i.e., WT::gltA(mt)-1 to 3), the DNA fragments including the gltA gene in the chromosome were amplified using the primers (SEQ ID NOS: 5 and 6) specified in Example 1. PCR was performed as follows: denaturation at 94° C. for 2 minutes; 30 cycles of denaturation at 94° C. for 1 minute, annealing at 56° C. for 1 minute, and polymerization at 72° C. for 40 seconds; and polymerization at 72° C. for 10 minutes.

The nucleotide sequences of the amplified genes were analyzed, and as a result, it was confirmed that these nucleotide sequences commonly showed the introduction of 1 to 2 modifications into the nucleotide sequence located 721 bp to 723 bp downstream of the gltA gene ORF initiation codon. That is, it was confirmed that the WT::gltA (mt)-1 to 3 strains were modified strains of citrate synthase (CS) in which the $721^{st}$ to the $723^{rd}$ nucleotide sequences are changed from the original 'AAC' to 'ACC' or 'ACT' (i.e., the change of the 241$^{st}$ amino acid from the N-terminus of the gltA gene from asparagine to threonine).

Example 4: Preparation of Various Strains in which the 241$^{st}$ Amino Acid of gltA Gene (i.e., Asparagine) is Substituted with Another Amino Acid An attempt was made to substitute the 241$^{st}$ amino acid in the amino acid sequence of SEQ ID NO: 1 (i.e., asparagine) (possessed by the wild-type strain) with an amino acid other than asparagine.

To introduce 19 kinds of modifications of heterogeneous nucleotide substitution including the N241T, which is the modification confirmed in Example 3, each recombinant vector was prepared as follows.

First, primers (SEQ ID NOS: 11 and 12), in which a recognition site of the restriction enzyme (XbaI) was inserted into the 5' fragment and the 3' fragment, respectively, about 600 bp apart either downstream or upstream from the positions of the 721$^{st}$ to the 723$^{rd}$ nucleotide sequences of the gltA gene, were synthesized using the genomic DNA extracted from the WT strain as a template. To introduce the 19 kinds of heterogeneous nucleotide-substituted modifications, primers (SEQ ID NOS: 13 to 48) for substituting the 721$^{st}$ to the 723$^{rd}$ nucleotide sequences of the gltA gene were synthesized (Table 3).

Specifically, the pDZ-gltA(N241A) plasmid was prepared in such a form that the DNA fragments (600 bp each) located at the 5' and 3' ends of the gltA gene were ligated to the pDZ vector (Korea Patent No. 2009-0094433). The 5' end gene fragment of the gltA gene was prepared by PCR using the chromosome of WT strain as a template along with primers (SEQ ID NOS: 11 and 13). PCR was performed as follows: denaturation at 94° C. for 2 minutes; 30 cycles of denaturation at 94° C. for 1 minute, annealing at 56° C. for 1 minute, and polymerization at 72° C. for 40 seconds; and polymerization at 72° C. for 10 minutes. Likewise, the 3' end gene fragment of the gltA gene was prepared by PCR using primers (SEQ ID NOS: 12 and 14). The amplified DNA fragments were purified using the PCR Purification kit (Quiagen) and used as insertion DNA fragments for the preparation of vectors.

Meanwhile, the insertion DNA fragments amplified by PCR and the pDZ vector, which was cleaved with a restriction enzyme (XbaI) and then heat-treated at 65° C. for 20 minutes, were ligated using the Infusion Cloning Kit and then transformed into E. coli DH5α. The strain was plated on a solid LB medium containing kanamycin (25 mg/L). The transformed colonies in which the target gene was inserted into the vector by PCR using the primers (SEQ ID NOS: 11 and 12) were selected, and the plasmid was obtained using a conventionally known plasmid extraction method and named as pDZ-gltA(N241A).

Likewise, plasmids were prepared as follows: the pDZ-gltA(N241V) using primers (SEQ ID NOS: 11 and 15 and SEQ ID NOS: 12 and 16); the pDZ-gltA(N241Q) using primers (SEQ ID NOS: 11 and 17 and SEQ ID NOS: 12 and 18); the pDZ-gltA(N241H) using primers (SEQ ID NOS: 11 and 19 and SEQ ID NOS: 12 and 20); the pDZ-gltA(N241R) using primers (SEQ ID NOS: 11 and 21 and SEQ ID NOS: 12 and 22); the pDZ-gltA(N241P) using primers (SEQ ID NOS: 11 and 23 and SEQ ID NOS: 12 and 24); the pDZ-gltA(N241L) using primers (SEQ ID NOS: 11 and 25 and SEQ ID NOS: 12 and 26); the pDZ-gltA(N241Y) using primers (SEQ ID NOS: 11 and 27 and SEQ ID NOS: 12 and 28); the pDZ-gltA(N241S) using primers (SEQ ID NOS: 11 and 29 and SEQ ID NOS: 12 and 30); the pDZ-gltA(N241K) using primers (SEQ ID NOS: 11 and 31 and SEQ ID NOS: 12 and 32); the pDZ-gltA(N241M) using primers (SEQ ID NOS: 11 and 33 and SEQ ID NOS: 12 and 34); the pDZ-gltA(N241I) using primers (SEQ ID NOS: 11 and 35 and SEQ ID NOS: 12 and 36); the pDZ-gltA(N241E) using primers (SEQ ID NOS: 11 and 37 and SEQ ID NOS: 12 and 38); the pDZ-gltA(N241D) using primers (SEQ ID NOS: 11 and 39 and SEQ ID NOS: 12 and 40); the pDZ-gltA(N241G) using primers (SEQ ID NOS: 11 and 41 and SEQ ID NOS: 12 and 42); the pDZ-gltA(N241W) using primers (SEQ ID NOS: 11 and 43 and SEQ ID NOS: 12 and 44); the pDZ-gltA(N241C) using primers (SEQ ID NOS: 11 and 45 and SEQ ID NOS: 12 and 46); the pDZ-gltA(N241F) using primers (SEQ ID NOS: 11 and 47 and SEQ ID NOS: 12 and 48); and the pDZ-gltA(N241T) using primers (SEQ ID NOS: 11 and 49 and SEQ ID NOS: 12 and 50).

TABLE 3

| Primer | Sequence (5'-> 3') |
|---|---|
| Primer (SEQ ID NO: 11) | CGGGGATCCTCTAGAAGATGCTGTCTGAGACTGGA |
| Primer (SEQ ID NO: 12) | CAGGTCGACTCTAGACGCTAAATTTAGCGCTCCTC |
| Primer (SEQ ID NO: 13) | GGAGGTGGAGCATGCCTGCTCGTGGTCAGC |
| Primer (SEQ ID NO: 14) | GACCACGAGCAGGCATGCTCCACCTCCACC |
| Primer (SEQ ID NO: 15) | GGAGGTGGAGCAGACCTGCTCGTGGTCAGC |
| Primer (SEQ ID NO: 16) | GACCACGAGCAGGTCTGCTCCACCTCCACC |
| Primer (SEQ ID NO: 17) | GGAGGTGGAGCACTGCTGCTCGTGGTCAGC |
| Primer (SEQ ID NO: 18) | GACCACGAGCAGCAGTGCTCCACCTCCACC |
| Primer (SEQ ID NO: 19) | GGAGGTGGAGCAGTGCTGCTCGTGGTCAGC |
| Primer (SEQ ID NO: 20) | GACCACGAGCAGCACTGCTCCACCTCCACC |
| Primer (SEQ ID NO: 21) | GGAGGTGGAGCAGCGCTGCTCGTGGTCAGC |
| Primer (SEQ ID NO: 22) | GACCACGAGCAGCGCTGCTCCACCTCCACC |
| Primer (SEQ ID NO: 23) | GGAGGTGGAGCATGGCTGCTCGTGGTCAGC |
| Primer (SEQ ID NO: 24) | GACCACGAGCAGCCATGCTCCACCTCCACC |
| Primer (SEQ ID NO: 25) | GGAGGTGGAGCACAGCTGCTCGTGGTCAGC |
| Primer (SEQ ID NO: 26) | GACCACGAGCAGCTGTGCTCCACCTCCACC |
| Primer (SEQ ID NO: 27) | GGAGGTGGAGCAGTACTGCTCGTGGTCAGC |

TABLE 3-continued

| Primer | Sequence (5'-> 3') |
|---|---|
| Primer (SEQ ID NO: 28) | GACCACGAGCAGTACTGCTCCACCTCCACC |
| Primer (SEQ ID NO: 29) | GGAGGTGGAGCAGGACTGCTCGTGGTCAGC |
| Primer (SEQ ID NO: 30) | GACCACGAGCAGTCCTGCTCCACCTCCACC |
| Primer (SEQ ID NO: 31) | GGAGGTGGAGCACTTCTGCTCGTGGTCAGC |
| Primer (SEQ ID NO: 32) | GACCACGAGCAGAAGTGCTCCACCTCCACC |
| Primer (SEQ ID NO: 33) | GGAGGTGGAGCACATCTGCTCGTGGTCAGC |
| Primer (SEQ ID NO: 34) | GACCACGAGCAGATGTGCTCCACCTCCACC |
| Primer (SEQ ID NO: 35) | GGAGGTGGAGCAGATCTGCTCGTGGTCAGC |
| Primer (SEQ ID NO: 36) | GACCACGAGCAGATCTGCTCCACCTCCACC |
| Primer (SEQ ID NO: 37) | GGAGGTGGAGCATTCCTGCTCGTGGTCAGC |
| Primer (SEQ ID NO: 38) | GACCACGAGCAGGAATGCTCCACCTCCACC |
| Primer (SEQ ID NO: 39) | GGAGGTGGAGCAGTCCTGCTCGTGGTCAGC |
| Primer (SEQ ID NO: 40) | GACCACGAGCAGGACTGCTCCACCTCCACC |
| Primer (SEQ ID NO: 41) | GGAGGTGGAGCAGCCCTGCTCGTGGTCAGC |
| Primer (SEQ ID NO: 42) | GACCACGAGCAGGGCTGCTCCACCTCCACC |
| Primer (SEQ ID NO: 43) | GGAGGTGGAGCAGCACTGCTCGTGGTCAGC |
| Primer (SEQ ID NO: 44) | GACCACGAGCAGTGGTGCTCCACCTCCACC |
| Primer (SEQ ID NO: 45) | GGAGGTGGAGCAGCACTGCTCGTGGTCAGC |
| Primer (SEQ ID NO: 46) | GACCACGAGCAGTGCTGCTCCACCTCCACC |
| Primer (SEQ ID NO: 47) | GGAGGTGGAGCAGAACTGCTCGTGGTCAGC |
| Primer (SEQ ID NO: 48) | GACCACGAGCAGTTCTGCTCCACCTCCACC |
| Primer (SEQ ID NO: 49) | GGAGGTGGAGCAGGTCTGCTCGTGGTCAGC |
| Primer (SEQ ID NO: 50) | GACCACGAGCAGACCTGCTCCACCTCCACC |

Each of the prepared vectors was transformed into the lysine-producing *Corynebacterium glutamicum* KCCM11016P strain (KR Patent No. 10-0159812) by the electric pulse method. The 19 strains in which a modification of heterogeneous nucleotide substitution was introduced to the gltA gene of each strain were named as follows: KCCM11016P::gltA(N241A), KCCM11016P::gltA(N241V), KCCM11016P::gltA(N241Q), KCCM11016P::gltA (N241H), KCCM11016P::gltA(N241R), KCCM11016P::gltA(N241P), KCCM11016P::gltA(N241L), KCCM110-16P::gltA(N241Y), KCCM11016P::gltA(N241S), KCCM-11016P::gltA(N241K), KCCM11016P::gltA(N241M), KCCM11016P::gltA(N241I), KCCM11016P::gltA(N24-1E), KCCM11016P::gltA(N241D), KCCM11016P::gltA (N241G), KCCM11016P::gltA(N241W), KCCM11016P::gltA(N241C), KCCM11016P::gltA(N241F), and KCC-M11016P::gltA(N241T).

Example 5: Analysis of Lysine Productivity and Measurement of Citrate Synthase (CS) Activity of gltA-Modified Strains The citrate synthase (CS) activity of the strains prepared in Example 4 was measured by the previously reported method (Ooyen et al., *Biotechnol. Bioeng.*, 109(8): 2070-2081, 2012). The gltA gene of the KCCM11016P strain was deleted by the method used in Example 1 and the resulting strain was named as KCCM11016P::ΔgltA. While using KCCM11016P and KCCM11016P::ΔgltA strains as the control groups, the selected 19 kinds of strains were cultured as described below, and the sugar consumption rate, production yield of lysine, concentration of glutamic acid (GA) (i.e., a representative by-product in the cultured medium), and CS enzyme activity were measured.

First, each of the strains was inoculated into a 250 mL corner-baffle flask containing 25 mL of a seed culture medium and cultured in a shaking incubator (200 rpm) at 30° C. for 20 hours. Then, each of the 250 mL corner-baffle flasks containing 24 mL of an L-lysine production medium was inoculated with 1 mL of a seed culture broth and cultured in a shaking incubator (200 rpm) at 32° C. for 72 hours. The compositions of the seed culture medium and the production medium are shown below. After the completion of the culture, the concentrations of L-lysine and glutamic acid in each culture were measured by HPLC (Waters 2478).

<Seed Culture Medium (pH 7.0)>
Glucose (20 g), Peptone (10 g), Yeast Extract (5 g), Urea (1.5 g), $KH_2PO_4$ (4 g), $K_2HPO_4$ (8 g), $MgSO_4.7H_2O$ (0.5 g), Biotin (100 μg), Thiamine.HCl (1,000 μg), Calcium-Pantothenic Acid (2,000 μg), Nicotinamide (2,000 μg) (based on 1 L of distilled water)

Production Medium (pH 7.0)>
Glucose (100 g), $(NH_4)_2SO_4$ 40 g, (40 g), Soybean Protein (2.5 g), Corn Steep Solids (5 g), Urea (3 g), $KH_2PO_4$ (1 g), $MgSO_4.7H_2O$ (0.5 g), Biotin (100 μg), Thiamine.HCl (1,000 μg), Calcium-Pantothenic Acid (2,000 μg), Nicotinamide (3,000 μg), and $CaCO3$ (30 g) (based on 1 L of distilled water)

To measure the CS enzyme activity, the cells were recovered by centrifugation, washed twice with 100 mM Tris-HCl buffer (pH 7.2, 3 mM L-cysteine, 10 mM $MgCl_2$), and the resultant was finally suspended in 2 mL of the same buffer. The cell suspension was physically disrupted for 10 minutes in a conventional glass bead vortexing method and the supernatant was recovered by two rounds of centrifugation (13,000 rpm, 4° C., 30 minutes) and used as a crude extract for the measurement of CS enzyme activity. To measure the CS enzyme activity, the crude extract was added to a reaction liquid for enzyme activity measurement (50 mM Tris, 200 mM potassium glutamate, pH 7.5, 0.1 mM 5,50-Dithiobis (2-nitrobenzoic acid, DTNB), 0.2 mM oxaloacetate, 0.15 mM acetyl-CoA) and reacted at 30° C. The CS activity was defined in terms of a ration by measuring the absorbance of DTNB, decomposed per minute relative to the parent strain, at 412 nm. The results of lysine-producing ability, sugar consumption rates, compositions of culture broth, and CS enzyme activity are shown in Table 4 below.

TABLE 4

Measurement of lysine-producing ability,, compositions of culture broth, and CS enzyme activity (%)

| Strain | CS Activity (%) | LYS Yield (%) | GA Concen- tration (mg/L) | sugar Consumption Rate (g/hr) |
|---|---|---|---|---|
| KCCM11016P | 100 | 43.4 | 436 | 4.53 |
| KCCM11016P::ΔgltA | 2 | 49.0 | 13 | 1.31 |
| KCCM11016P::gltA(N241A) | 36 | 46.2 | 430 | 3.56 |
| KCCM11016P::gltA(N241V) | 61 | 44.8 | 428 | 4.08 |
| KCCM11016P::gltA(N241Q) | 91 | 43.9 | 386 | 4.21 |
| KCCM11016P::gltA(N241H) | 57 | 44.0 | 431 | 4.33 |
| KCCM11016P::gltA(N241R) | 86 | 43.5 | 432 | 4.68 |
| KCCM11016P::gltA(N241P) | 71 | 43.9 | 411 | 4.66 |
| KCCM11016P::gltA(N241L) | 79 | 44.7 | 429 | 4.51 |
| KCCM11016P::gltA(N241Y) | 35 | 46.9 | 373 | 4.59 |
| KCCM11016P::gltA(N241S) | 36 | 46.8 | 391 | 4.48 |
| KCCM11016P::gltA(N241K) | 61 | 44.1 | 409 | 4.19 |
| KCCM11016P::gltA(N241M) | 52 | 44.0 | 412 | 3.89 |
| KCCM11016P::gltA(N241I) | 41 | 46.5 | 422 | 3.65 |
| KCCM11016P::gltA(N241E) | 51 | 43.8 | 401 | 3.90 |
| KCCM11016P::gltA(N241D) | 40 | 46.1 | 399 | 3.51 |
| KCCM11016P::gltA(N241G) | 71 | 44.9 | 418 | 4.12 |
| KCCM11016P::gltA(N241W) | 45 | 46.2 | 308 | 3.54 |
| KCCM11016P::gltA(N241C) | 46 | 46.6 | 310 | 3.69 |
| KCCM11016P::gltA(N241F) | 48 | 45.7 | 386 | 4.09 |
| KCCM11016P::gltA(N241T) | 31 | 48.6 | 351 | 4.51 |

In the case of a strain where the gltA gene is deleted, the lysine yield of the strain showed an increase of about 5.5% p compared to that of its parent strain, but the strain was unable to consume sugar until the later stage of the cultivation. That is, in the case where the gltA gene is deleted and thus the strain has almost no CS activity, the growth of the strain is inhibited thus making the industrial application of the strain difficult. It was confirmed that in all cases where the strain included a modified polypeptide in which the $241^{st}$ amino acid in the amino acid sequence of SEQ ID NO: 1 was substituted with a different amino acid, the CS activity was attenuated while the growth of the strain was maintained at an industrially applicable level. Additionally, as the CS activity of the strain was attenuated, the lysine yield of the strain tended to increase by about 3% p to 5% p compared to that of its parent strain. In particular, in the cases of three modified strains (i.e., N241S, N241Y, and N241T) among the modified strains in which the CS activity was attenuated to a 30% to 60% level, these strains showed an increase in the lysine yield by about 3% p to 5% p compared to that of their parent strain while showing similar levels in the sugar consumption rate. Additionally, it was confirmed that the strains where the lysine yield was increased compared to that of their parent strain showed a decrease in the amount of glutamic acid (GA) in the culture broth. That is, it was interpreted that the introduction of a modification of the present disclosure into these strains has an effect of improving the lysine yield of these strains while reducing the by-products of these strains.

These results show that the amount of lysine production can be increased via an appropriate balance between the carbon-flow into the TCA pathway and the amount of oxaloacetate (i.e., a precursor of lysine biosynthesis) supply. In particular, considering that the amount of glutamic acid, which is normally produced as a by-product in a large amount during lysine cultivation, was reduced, it was confirmed that the attenuation of the gltA gene activity inhibits the carbon-flow into the TCA pathway and thereby induces the carbon-flow into the direction of lysine biosynthesis thus being significantly effective in increasing the lysine productivity.

Among the strains prepared above, the KCCM11016P::gltA(N241T) strain was deposited on Nov. 20, 2017, to the Korean Collection for Korean Culture Center of Microorganisms (KCCM), an international depositary authority under the Budapest Treaty, and assigned Accession Number KCCM12154P.

Example 6: Analysis of Lysine-Producing Ability of Selected gltA-Modified Strains The modifications of three gltA-modified strains selected in Example 5 were introduced into L-lysine-producing *Corynebacterium glutamicum* strains (i.e., KCCM10770P (KR Patent No. 10-0924065) and KCCM11347P (KR Patent No. 10-0073610)). These three strains were selected based on the criteria that they have reduced CS activity, have a sugar consumption rate similar to that of their parent strain, and an increased lysine yield compared to that of their parent strain. The three kinds of vectors of Example 4 (i.e., pDZ-gltA(N241S), pDZ-gltA(N241Y), and pDZ-gltA(N241T)) were introduced into the two *Corynebacterium glutamicum* strains (i.e., KCCM10770P and KCCM11347P) by the electric pulse method to prepare six strains (i.e., KCCM10770P::gltA (N241S), KCCM10770P::gltA(N241Y), KCCM-10770P::gltA(N241T), KCCM11347P::gltA(N241S), KCCM11347P::gltA(N241Y), and KCCM11347P::gltA(N241T)). The two control group strains (i.e., KCCM10770P and KCCM11347P) and the six strains with modifications of nucleotide substitution in the gltA gene were cultured in the same manner as in Example 5, and the lysine-producing ability, sugar consumption rate, and composition of the culture liquid of these strains were analyzed.

After culturing these strains for a certain period of time, the lysine producing ability, sugar consumption rate and the composition of culture broth were analyzed. The results are shown in Table 5 below.

TABLE 5

Analysis of lysine producing ability, sugar consumption rate and the composition of culture broth, of gltA-modified strains

| Strain | LYS Yield (%) | GA Concentration (mg/L) | Sugar Consumption Rate (g/hr) |
|---|---|---|---|
| KCCM10770P | 42.6 | 406 | 4.27 |
| KCCM10770P::gltA(N241S) | 46.4 | 350 | 4.08 |
| KCCM10770P::gltA(N241Y) | 45.9 | 368 | 4.20 |
| KCCM10770P::gltA(N241T) | 48.0 | 240 | 4.04 |
| KCCM11347P | 38.3 | 440 | 5.99 |
| KCCM11347P::gltA(N241S) | 41.7 | 386 | 5.85 |
| KCCM11347P::gltA(N241Y) | 42.1 | 402 | 5.96 |
| KCCM11347P::gltA(N241T) | 43.5 | 316 | 5.84 |

As shown in the results of Table 5 above, in the cases of two lysine-producing strains (i.e., KCCM10770P and KCCM11347P) where a modification that the $241^{st}$ amino acid of the gltA sequence was substituted with another amino acid, all of the strains showed an increased lysine production yield, a decreased yield of by-products, and a similar sugar consumption rate compared to that of their parent strain. It was confirmed that among the three kinds of modifications, the strain having the modification (N241T) (i.e., a modification where the 241$^{st}$ amino acid (asparagine) was substituted with threonine) showed the highest increase in lysine yield while showing a similar level or slightly increased level of sugar consumption rate compared to that of their parent strain. Additionally, it was confirmed that the N241T modification showed the highest level of decrease in glutamic acid yield. From these results, it was confirmed that the attenuation of the gltA gene activity resulted in the decrease into the TCA pathway thereby causing a decrease in the amount of glutamic acid in the culture broth, as confirmed in the results of Example 6.

Example 7: Preparation and Analysis of Lysine-Producing Ability of CJ3P Strain in which gltA-Modification (N241T) is Introduced To confirm whether other L-lysine-producing *Corynebacterium glutamicum* strains also have the same effect described above, a strain in which a gltA(N241T) modification was introduced was prepared using the *Corynebacterium glutamicum* CJ3P (Binder et al. *Genome Biology,* 2012, 13:R40) that is provided with the L-lysine-producing ability by the introduction of three kinds of modifications [i.e., pyc(P458S), hom(V59A), and lysC(T311I)] to the wild-type strain in the same manner as in Example 6. The thus prepared strain was named as CJ3::gltA(N241T). The control groups (i.e., CJ3P and CJ3::gltA(N241T) strains) were cultured in the same manner as in Example 5, and the lysine producing ability, sugar consumption rate and the composition of culture broth are analyzed and the results are shown in Table 6 below.

TABLE 6

Analysis of lysine producing ability, sugar consumption rate and the composition of culture broth of CJ3P-derived gltA-modified strains

| Strain | LYS Yield (%) | GA Concentration (mg/L) | Sugar Consumption Rate (g/hr) |
|---|---|---|---|
| CJ3P | 9.2 | 2689 | 5.86 |
| CJ3P::gltA(N241T) | 13.5 | 1983 | 5.51 |

As a result of the analysis of lysine producing ability, sugar consumption rate and the composition of culture broth, it was confirmed that the strain where the modification of gltA(N241T)) was introduced showed an increase of lysine yield and a decrease in the concentration of glutamic acid while maintaining the sugar consumption rate at a similar level.

Example 8: Preparation of Threonine Strain in which gltA-Modification (N241T) is Introduced and Analysis of Threonine-Producing Ability To explicitly confirm the changes in the L-threonine-producing ability by the introduction of the gltA(N241T) modification, the gene encoding homoserine dehydrogenase that produces homoserine (i.e., a common intermediate in the biosynthesis pathways of L-threonine and L-isoleucine) was overexpressed by the modification. Specifically, a strain, in which a known hom(G378E) modification (R. Winkels, S. et al., *Appl. Microbiol. Biotechnol.* 45, 612-620, 1996) was introduced into the CJ3P::gltA(N241T) strain used in Example 7, was prepared. Additionally, a strain, in which only the hom(G378E) modification was introduced to the CJ3P, was prepared as the control group. Recombinant vectors for the introduction of modifications were prepared by the method described below.

To prepare a vector for the introduction of hom(G378E), first, primers (SEQ ID NO: 51 and 52), in which a recognition site of the restriction enzyme (XbaI) was inserted into the 5'-end fragment and the 3'-end fragment, respectively, about 600 bp apart either downstream or upstream from the positions of the 1,131$^{st}$ to the 1,134$^{th}$ nucleotide sequences of the hom gene, were synthesized using the genomic DNA extracted from the WT strain as a template. Primers (SEQ ID NO: 53 and 54) for substituting the nucleotide sequence of the hom gene (Table 7). The pDZ-hom(G378E) plasmid was prepared in a form where the DNA fragments (600 bp each) located at each of the 5' and 3' ends was connected to the pDZ vector (Korea Patent No. 2009-0094433). The 5'-end fragment of the hom gene was prepared by PCR using the chromosome of the WT strain as a template along with primers (SEQ ID NO: 51 and 53). PCR was performed as follows: denaturation at 94° C. for 2 minutes; 30 cycles of denaturation at 94° C. for 1 minute, annealing at 56° C. for 1 minute, and polymerization at 72° C. for 40 seconds; and polymerization at 72° C. for 10 minutes. Likewise, 3'-end fragment of the hom gene was prepared by PCR using primers (SEQ ID NO: 52 and 54). The amplified DNA fragment was purified using the PCR Purification kit (Quiagen) and used as the insertion DNA fragment for vector preparation. Meanwhile, the pDZ vector, which was treated with the restriction enzyme XbaI and heat treated at 65° C. for 20 minutes, was ligated to the insertion DNA fragment amplified by PCR using the Infusion Cloning Kit, and the ligated product was transformed into *E. coli* DH5a and plated on a solid LB medium containing kanamycin (25 mg/L). The colonies, transformed with a vector in which the target gene obtained by PCR using primers (SEQ ID NO: 51 and 52) was inserted, were selected and the plasmid was obtained by a conventionally known plasmid extraction method, and thereby a vector for the introduction of a modification of nucleotide substitution of hom(G378E) on the chromosome (i.e., pDZ-hom(G378E)) was prepared.

TABLE 7

| Primer | Sequence (5' -> 3') |
|---|---|
| Primer (SEQ ID NO: 51) | TCCTCTAGACTGGTCGCCTGATGTTCTAC |
| Primer (SEQ ID NO: 52) | GACTCTAGATTAGTCCCTTTCGAGGCGGA |
| Primer (SEQ ID NO: 53) | GCCAAAACCTCCACGCGATC |
| Primer (SEQ ID NO: 54) | ATCGCGTGGAGGTTTTGGCT |

Strains in which a nucleotide modification is introduced in the hom gene in the CJ3P and CJ3P::gltA(N241T) strains by the pDZ-hom(G378E) vector using the method same as in Example 6 (i.e., CJ3P::hom(G378E) and CJ3P::gltA (N241T)-hom(G378E)) were obtained. The obtained two kinds of strains were cultured using the method same as in Example 5, and the concentration of threonine, sugar consumption rate and composition of the culture broth were analyzed. The results are shown in Table 8 below.

TABLE 8

Concentration of threonine, sugar consumption rate, and composition of culture broth.

| Strain | Thr Concentration (g/L) | GA Concentration (mg/L) | Sugar Consumption Rate (g/hr) |
|---|---|---|---|
| CJ3P::hom(G378E) | 2.8 | 2769 | 5.36 |
| CJ3P::gltA(N241T)-hom(G378E) | 6.1 | 1891 | 5.17 |

As a result of the analysis of the concentration of threonine, sugar consumption rate and composition of the culture broth, it was confirmed that the threonine concentration increased at a similar level of sugar consumption rate while the glutamic acid concentration decreased, in the strain where the modification of gltA(N241T) was introduced.

Example 9: Preparation of Isoleucine Strain where gltA-Modification (N241T) is Introduced and Analysis of Isoleucine-Producing Ability To confirm the effect of the introduction of the gltA (N241T) modification on the L-isoleucine-producing ability, the gene encoding L-threonine dehydratase was also overexpressed by the previously reported modification. Specifically, a strain, in which a known ilvA(V323A) modification (S. Morbach et al., *Appl. Enviro. Microbiol.*, 62(12): 4345-4351, 1996) was introduced into the CJ3P::gltA(N241T)-hom(G378E) strain used in Example 7, was prepared. Additionally, a strain, in which only the ilvA(V323A) modification was introduced to the CJ3P::hom(G378E), was prepared as the control group. Recombinant vectors for the introduction of modifications were prepared by the method described below.

To prepare a vector for the introduction of ilvA(V323A), first, primers (SEQ ID NO: 55 and 56), in which a recognition site of the restriction enzyme (XbaI) was inserted into the 5'-end fragment and the 3'-end fragment, respectively, about 600 bp apart either downstream or upstream from the positions of the $966^{st}$ to the $969^{th}$ nucleotide sequences of the ilvA gene, were synthesized using the genomic DNA extracted from the WT strain as a template. Additionally, primers (SEQ ID NO: 57 and 58) for substituting the nucleotide sequence of the ilvA gene (Table 9). The pDZ-ilvA(V323A) plasmid was prepared in a form where the DNA fragments (600 bp each) located at each of the 5' and 3' ends was connected to the pDZ vector (Korea Patent No. 2009-0094433). The 5'-end fragment of the ilvA gene was prepared by PCR using the chromosome of the WT strain as a template along with primers (SEQ ID NO: 55 and 57). PCR was performed as follows: denaturation at 94° C. for 2 minutes; 30 cycles of denaturation at 94° C. for 1 minute, annealing at 56° C. for 1 minute, and polymerization at 72° C. for 40 seconds; and polymerization at 72° C. for 10 minutes.

Likewise, 3'-end fragment of the ilvA gene was prepared by PCR using primers (SEQ ID NO: 56 and 58). The amplified DNA fragment was purified using the PCR Purification kit (Quiagen) and used as the insertion DNA fragment for vector preparation. Meanwhile, the pDZ vector, which was treated with the restriction enzyme XbaI and heat treated at 65° C. for 20 minutes, was ligated to the insertion DNA fragment amplified by PCR using the Infusion Cloning Kit, and the ligated product was transformed into *E. coli* DH5a and plated on a solid LB medium containing kanamycin (25 mg/L). The colonies, transformed with a vector in which the target gene obtained by PCR using primers (SEQ ID NO: 55 and 56) was inserted, were selected and the plasmid was obtained by a conventionally known plasmid extraction method, and thereby a vector for the introduction of a modification of nucleotide substitution of ilvA(V323A) on the chromosome (i.e., pDZ-ilvA(V323A)) was prepared.

TABLE 9

| Primer | Sequence (5'-> 3') |
|---|---|
| Primer (SEQ ID NO: 55) | ACGGATCCCAGACTCC AAAGCAAAAGCG |
| Primer (SEQ ID NO: 56) | ACGGATCCAACCAAAC TTGCTCACACTC |
| SEQ ID NO: 57) | ACACCACGGCAGAACC AGGTGCAAAGGACA |
| Primer (SEQ ID NO: 58) | CTGGTTCTGCCGTGGT GTGCATCATCTCTG |

Strains in which a nucleotide modification is introduced in the ilvA gene in the CJ3P::hom(G378E) and CJ3P::gltA (N241T)-hom(G378E) strains by the pDZ-ilvA(G378E) vector using the method same as in Example 6 (i.e., CJ3P::hom(G378E)-ilvA(V323A) and CJ3P::gltA(N241T)-hom (G378E)-ilvA(V323A)) were obtained. The obtained two kinds of strains were cultured using the method same as in Example 5, and the concentration of isoleucine and GA of the culture broth and sugar consumption rate were analyzed. The results are shown in Table 10 below.

TABLE 10

Concentration of isoleucine, sugar consumption rate and composition of culture broth

| Strain | Ile Concentration (g/L) | GA Concentration (mg/L) | Sugar Consumption Rate (g/hr) |
|---|---|---|---|
| CJ3P::hom(G378E)-ilvA(V323A) | 0.5 | 2912 | 4.92 |
| CJ3P::gltA(N241T)-hom(G378E)-ilvA(V323A) | 1.6 | 2006 | 5.13 |

As a result of the analysis of the concentration of threonine, sugar consumption rate and composition of culture broth, it was confirmed that the isoleucine concentration increased at a similar level of sugar consumption rate while the glutamic acid concentration decreased, in the strain where the modification of gltA(N241T) was introduced.

From the foregoing, a skilled person in the art to which the present disclosure pertains will be able to understand that the present disclosure may be embodied in other specific forms without modifying the technical concepts or essential characteristics of the present disclosure. In this regard, the exemplary embodiments disclosed herein are only for illustrative purposes and should not be construed as limiting the scope of the present disclosure. On the contrary, the present disclosure is intended to cover not only the exemplary embodiments but also various alternatives, modifications, equivalents, and other embodiments that may be included within the spirit and scope of the present disclosure as defined by the appended claims.

The invention claimed is:

1. A modified polypeptide having citrate synthase activity, wherein the 241st amino acid in the amino acid sequence of SEQ ID NO: 1, asparagine, is substituted with another amino acid, and wherein the modified polypeptide has attenuated citrate synthase activity compared to the unmodified polypeptide.

2. The modified polypeptide according to claim 1, wherein the 241st amino acid, asparagine, is substituted with an amino acid other than lysine.

3. The modified polypeptide according to claim 1, wherein the another amino acid is an aromatic amino acid or a hydrophilic amino acid.

4. The modified polypeptide according to claim 1, wherein the 241st amino acid, asparagine, is substituted with threonine, serine, or tyrosine.

5. A microorganism of the genus *Corynebacterium* comprising the modified polypeptide of claim 1.

6. The microorganism according to claim 5, wherein the microorganism of the genus *Corynebacterium* produces an L-amino acid.

7. The microorganism according to claim 5, wherein the microorganism of the genus *Corynebacterium* produces an aspartate-derived L-amino acid.

8. The microorganism according to claim 5, wherein the microorganism of the genus *Corynebacterium* produces at least one L-amino acid selected from the group consisting of lysine, threonine, methionine, homoserine or a derivative thereof, and isoleucine.

9. The microorganism according to claim 5, wherein the microorganism of the genus *Corynebacterium* is *Corynebacterium glutamicum*.

\* \* \* \* \*

SEQUENCE LISTING

<160> NUMBER OF SEQ ID NOS: 62

<210> SEQ ID NO 1
<211> LENGTH: 437
<212> TYPE: PRT
<213> ORGANISM: Corynebacterium glutamicum
<220> FEATURE:
<221> NAME/KEY: PEPTIDE
<222> LOCATION: (1)...(437)
<223> OTHER INFORMATION: gltA

<400> SEQUENCE: 1

```
Met Phe Glu Arg Asp Ile Val Ala Thr Asp Asn Asn Lys Ala Val Leu
 1               5                  10                  15

His Tyr Pro Gly Gly Glu Phe Glu Met Asp Ile Ile Glu Ala Ser Glu
            20                  25                  30

Gly Asn Asn Gly Val Val Leu Gly Lys Met Leu Ser Glu Thr Gly Leu
        35                  40                  45

Ile Thr Phe Asp Pro Gly Tyr Val Ser Thr Gly Ser Thr Glu Ser Lys
50                  55                  60

Ile Thr Tyr Ile Asp Gly Asp Ala Gly Ile Leu Arg Tyr Arg Gly Tyr
65                  70                  75                  80

Asp Ile Ala Asp Leu Ala Glu Asn Ala Thr Phe Asn Glu Val Ser Tyr
                85                  90                  95

Leu Leu Ile Asn Gly Glu Leu Pro Thr Pro Asp Glu Leu His Lys Phe
            100                 105                 110

Asn Asp Glu Ile Arg His His Thr Leu Leu Asp Glu Asp Phe Lys Ser
        115                 120                 125

Gln Phe Asn Val Phe Pro Arg Asp Ala His Pro Met Ala Thr Leu Ala
130                 135                 140

Ser Ser Val Asn Ile Leu Ser Thr Tyr Tyr Gln Asp Gln Leu Asn Pro
145                 150                 155                 160

Leu Asp Glu Ala Gln Leu Asp Lys Ala Thr Val Arg Leu Met Ala Lys
                165                 170                 175

Val Pro Met Leu Ala Ala Tyr Ala His Arg Ala Arg Lys Gly Ala Pro
            180                 185                 190

Tyr Met Tyr Pro Asp Asn Ser Leu Asn Ala Arg Glu Asn Phe Leu Arg
        195                 200                 205

Met Met Phe Gly Tyr Pro Thr Glu Pro Tyr Glu Ile Asp Pro Ile Met
210                 215                 220

Val Lys Ala Leu Asp Lys Leu Leu Ile Leu His Ala Asp His Glu Gln
225                 230                 235                 240

Asn Cys Ser Thr Ser Thr Val Arg Met Ile Gly Ser Ala Gln Ala Asn
                245                 250                 255

Met Phe Val Ser Ile Ala Gly Gly Ile Asn Ala Leu Ser Gly Pro Leu
            260                 265                 270

His Gly Gly Ala Asn Gln Ala Val Leu Glu Met Leu Glu Asp Ile Lys
        275                 280                 285

Ser Asn His Gly Gly Asp Ala Thr Glu Phe Met Asn Lys Val Lys Asn
290                 295                 300

Lys Glu Asp Gly Val Arg Leu Met Gly Phe Gly His Arg Val Tyr Lys
305                 310                 315                 320

Asn Tyr Asp Pro Arg Ala Ala Ile Val Lys Glu Thr Ala His Glu Ile
                325                 330                 335

Leu Glu His Leu Gly Gly Asp Asp Leu Leu Asp Leu Ala Ile Lys Leu
            340                 345                 350
```

Glu Glu Ile Ala Leu Ala Asp Asp Tyr Phe Ile Ser Arg Lys Leu Tyr
        355                 360                 365

Pro Asn Val Asp Phe Tyr Thr Gly Leu Ile Tyr Arg Ala Met Gly Phe
    370                 375                 380

Pro Thr Asp Phe Phe Thr Val Leu Phe Ala Ile Gly Arg Leu Pro Gly
385                 390                 395                 400

Trp Ile Ala His Tyr Arg Glu Gln Leu Gly Ala Ala Gly Asn Lys Ile
                405                 410                 415

Asn Arg Pro Arg Gln Val Tyr Thr Gly Asn Glu Ser Arg Lys Leu Val
            420                 425                 430

Pro Arg Glu Glu Arg
        435

<210> SEQ ID NO 2
<211> LENGTH: 1314
<212> TYPE: DNA
<213> ORGANISM: Corynebacterium glutamicum
<220> FEATURE:
<221> NAME/KEY: gene
<222> LOCATION: (1)...(1314)
<223> OTHER INFORMATION: gltA

<400> SEQUENCE: 2

```
atgtttgaaa gggatatcgt ggctactgat aacaacaagg ctgtcctgca ctaccccggt      60
ggcgagttcg aaatggacat catcgaggct tctgagggta caacggtgt tgtcctgggc     120
aagatgctgt ctgagactgg actgatcact tttgacccag ttatgtgag cactggctcc     180
accgagtcga agatcaccta tcgatggc gatgcgggaa tcctgcgtta ccgcggctat      240
gacatcgctg atctggctga aatgccacc ttcaacgagg tttcttacct acttatcaac     300
ggtgagctac caaccccaga tgagcttcac aagtttaacg acgagattcg ccaccacacc    360
cttctggacg aggacttcaa gtcccagttc aacgtgttcc cacgcgacgc tcacccaatg    420
gcaaccttgg cttcctcggt taacattttg tctacctact accaggacca gctgaaccca    480
ctcgatgagg cacagcttga taaggcaacc gttcgcctca tggcaaaggt tccaatgctg    540
gctgcgtacg cacaccgcgc acgcaagggt gctccttaca tgtacccaga caactccctc    600
aatgcgcgtg agaacttcct gcgcatgatg ttcggttacc caaccgagcc atacgagatc    660
gacccaatca tggtcaaggc tctggacaag ctgctcatcc tgcacgctga ccacgagcag    720
aactgctcca cctccaccgt tcgtatgatc ggttccgcac aggccaacat gtttgtctcc    780
atcgctggtg gcatcaacgc tctgtccggc ccactgcacg gtggcgcaaa ccaggctgtt    840
ctggagatgc tcgaagacat caagagcaac acggtggcg acgcaaccga gttcatgaac    900
aaggtcaaga caaggaaga cggcgtccgc tcatgggct tcggacaccg cgtttacaag    960
aactacgatc cacgtgcagc aatcgtcaag gagaccgcac acgagatcct cgagcacctc   1020
ggtggcgacg atcttctgga tctggcaatc aagctggaag aaattgcact ggctgatgat  1080
tacttcatct cccgcaagct ctacccgaac gtagacttct acaccggcct gatctaccgc   1140
gcaatgggct tcccaactga cttcttcacc gtattgttcg caatcggtcg tctgccagga   1200
tggatcgctc actaccgcga gcagctcggt gcagcaggca caagatcaa ccgcccacgc   1260
caggtctaca ccggcaacga atcccgcaag ttggttcctc gcgaggagcg ctaa         1314
```

<210> SEQ ID NO 3
<211> LENGTH: 437
<212> TYPE: PRT

<213> ORGANISM: Unknown
<220> FEATURE:
<223> OTHER INFORMATION: N241T

<400> SEQUENCE: 3

```
Met Phe Glu Arg Asp Ile Val Ala Thr Asp Asn Asn Lys Ala Val Leu
1               5                   10                  15

His Tyr Pro Gly Gly Glu Phe Glu Met Asp Ile Ile Glu Ala Ser Glu
            20                  25                  30

Gly Asn Asn Gly Val Val Leu Gly Lys Met Leu Ser Glu Thr Gly Leu
        35                  40                  45

Ile Thr Phe Asp Pro Gly Tyr Val Ser Thr Gly Ser Thr Glu Ser Lys
50                  55                  60

Ile Thr Tyr Ile Asp Gly Asp Ala Gly Ile Leu Arg Tyr Arg Gly Tyr
65                  70                  75                  80

Asp Ile Ala Asp Leu Ala Glu Asn Ala Thr Phe Asn Glu Val Ser Tyr
                85                  90                  95

Leu Leu Ile Asn Gly Glu Leu Pro Thr Pro Asp Glu Leu His Lys Phe
            100                 105                 110

Asn Asp Glu Ile Arg His His Thr Leu Leu Asp Glu Asp Phe Lys Ser
        115                 120                 125

Gln Phe Asn Val Phe Pro Arg Asp Ala His Pro Met Ala Thr Leu Ala
130                 135                 140

Ser Ser Val Asn Ile Leu Ser Thr Tyr Tyr Gln Asp Gln Leu Asn Pro
145                 150                 155                 160

Leu Asp Glu Ala Gln Leu Asp Lys Ala Thr Val Arg Leu Met Ala Lys
                165                 170                 175

Val Pro Met Leu Ala Ala Tyr Ala His Arg Ala Arg Lys Gly Ala Pro
            180                 185                 190

Tyr Met Tyr Pro Asp Asn Ser Leu Asn Ala Arg Glu Asn Phe Leu Arg
        195                 200                 205

Met Met Phe Gly Tyr Pro Thr Glu Pro Tyr Glu Ile Asp Pro Ile Met
210                 215                 220

Val Lys Ala Leu Asp Lys Leu Leu Ile Leu His Ala Asp His Glu Gln
225                 230                 235                 240

Thr Cys Ser Thr Ser Thr Val Arg Met Ile Gly Ser Ala Gln Ala Asn
                245                 250                 255

Met Phe Val Ser Ile Ala Gly Gly Ile Asn Ala Leu Ser Gly Pro Leu
            260                 265                 270

His Gly Gly Ala Asn Gln Ala Val Leu Glu Met Leu Glu Asp Ile Lys
        275                 280                 285

Ser Asn His Gly Gly Asp Ala Thr Glu Phe Met Asn Lys Val Lys Asn
290                 295                 300

Lys Glu Asp Gly Val Arg Leu Met Gly Phe Gly His Arg Val Tyr Lys
305                 310                 315                 320

Asn Tyr Asp Pro Arg Ala Ala Ile Val Lys Glu Thr Ala His Glu Ile
                325                 330                 335

Leu Glu His Leu Gly Gly Asp Asp Leu Leu Asp Leu Ala Ile Lys Leu
            340                 345                 350

Glu Glu Ile Ala Leu Ala Asp Asp Tyr Phe Ile Ser Arg Lys Leu Tyr
        355                 360                 365

Pro Asn Val Asp Phe Tyr Thr Gly Leu Ile Tyr Arg Ala Met Gly Phe
370                 375                 380

Pro Thr Asp Phe Phe Thr Val Leu Phe Ala Ile Gly Arg Leu Pro Gly
```

```
                385                 390                 395                 400
Trp Ile Ala His Tyr Arg Glu Gln Leu Gly Ala Ala Gly Asn Lys Ile
                    405                 410                 415

Asn Arg Pro Arg Gln Val Tyr Thr Gly Asn Glu Ser Arg Lys Leu Val
                420                 425                 430

Pro Arg Glu Glu Arg
        435
```

<210> SEQ ID NO 4
<211> LENGTH: 1314
<212> TYPE: DNA
<213> ORGANISM: Unknown
<220> FEATURE:
<223> OTHER INFORMATION: N241T

<400> SEQUENCE: 4

| | | | | | |
|---|---|---|---|---|---|
| atgtttgaaa | gggatatcgt | ggctactgat | aacaacaagg | ctgtcctgca | ctaccccggt | 60 |
| ggcgagttcg | aaatggacat | catcgaggct | tctgagggta | acaacggtgt | tgtcctgggc | 120 |
| aagatgctgt | ctgagactgg | actgatcact | tttgacccag | gttatgtgag | cactggctcc | 180 |
| accgagtcga | agatcaccta | catcgatggc | gatgcgggaa | tcctgcgtta | ccgcggctat | 240 |
| gacatcgctg | atctggctga | gaatgccacc | ttcaacgagg | tttcttacct | acttatcaac | 300 |
| ggtgagctac | caaccccaga | tgagcttcac | aagtttaacg | acgagattcg | ccaccacacc | 360 |
| cttctggacg | aggacttcaa | gtcccagttc | aacgtgttcc | cacgcgacgc | tcacccaatg | 420 |
| gcaaccttgg | cttcctcggt | taacattttg | tctacctact | accaggacca | gctgaaccca | 480 |
| ctcgatgagg | cacagcttga | taaggcaacc | gttcgcctca | tggcaaaggt | tccaatgctg | 540 |
| gctgcgtacg | cacaccgcgc | acgcaagggt | gctccttaca | tgtacccaga | caactccctc | 600 |
| aatgcgcgtg | agaacttcct | gcgcatgatg | ttcggttacc | caaccgagcc | atacgagatc | 660 |
| gacccaatca | tggtcaaggc | tctggacaag | ctgctcatcc | tgcacgctga | ccacgagcag | 720 |
| acctgctcca | cctccaccgt | tcgtatgatc | ggttccgcac | aggccaacat | gtttgtctcc | 780 |
| atcgctggtg | gcatcaacgc | tctgtccggc | ccactgcacg | gtggcgcaaa | ccaggctgtt | 840 |
| ctggagatgc | tcgaagacat | caagagcaac | acggtggcg | acgcaaccga | gttcatgaac | 900 |
| aaggtcaaga | acaaggaaga | cggcgtccgc | ctcatgggct | tcggacaccg | cgtttacaag | 960 |
| aactacgatc | cacgtgcagc | aatcgtcaag | gagaccgcac | acgagatcct | cgagcacctc | 1020 |
| ggtggcgacg | atcttctgga | tctggcaatc | aagctggaag | aaattgcact | ggctgatgat | 1080 |
| tacttcatct | cccgcaagct | ctacccgaac | gtagacttct | acaccggcct | gatctaccgc | 1140 |
| gcaatgggct | tcccaactga | cttcttcacc | gtattgttcg | caatcggtcg | tctgccagga | 1200 |
| tggatcgctc | actaccgcga | gcagctcggt | gcagcaggca | acaagatcaa | ccgcccacgc | 1260 |
| caggtctaca | ccggcaacga | atcccgcaag | ttggttcctc | gcgaggagcg | ctaa | 1314 |

<210> SEQ ID NO 5
<211> LENGTH: 21
<212> TYPE: DNA
<213> ORGANISM: Artificial Sequence
<220> FEATURE:
<223> OTHER INFORMATION: primer

<400> SEQUENCE: 5
atgtttgaaa gggatatcgt g                                        21

<210> SEQ ID NO 6

```
<211> LENGTH: 21
<212> TYPE: DNA
<213> ORGANISM: Artificial Sequence
<220> FEATURE:
<223> OTHER INFORMATION: primer

<400> SEQUENCE: 6
ttagcgctcc tcgcgaggaa c                                          21

<210> SEQ ID NO 7
<211> LENGTH: 30
<212> TYPE: DNA
<213> ORGANISM: Artificial Sequence
<220> FEATURE:
<223> OTHER INFORMATION: primer

<400> SEQUENCE: 7
cggggatcct ctagacgatg aaaaacgccc                                 30

<210> SEQ ID NO 8
<211> LENGTH: 30
<212> TYPE: DNA
<213> ORGANISM: Artificial Sequence
<220> FEATURE:
<223> OTHER INFORMATION: primer

<400> SEQUENCE: 8
caggtcgact ctagactgca cgtggatcgt                                 30

<210> SEQ ID NO 9
<211> LENGTH: 24
<212> TYPE: DNA
<213> ORGANISM: Artificial Sequence
<220> FEATURE:
<223> OTHER INFORMATION: primer

<400> SEQUENCE: 9
actgggacta tttgttcgga aaaa                                       24

<210> SEQ ID NO 10
<211> LENGTH: 24
<212> TYPE: DNA
<213> ORGANISM: Artificial Sequence
<220> FEATURE:
<223> OTHER INFORMATION: primer

<400> SEQUENCE: 10
cgaacaaata gtcccagttc aacg                                       24

<210> SEQ ID NO 11
<211> LENGTH: 35
<212> TYPE: DNA
<213> ORGANISM: Artificial Sequence
<220> FEATURE:
<223> OTHER INFORMATION: primer

<400> SEQUENCE: 11
cggggatcct ctagaagatg ctgtctgaga ctgga                           35

<210> SEQ ID NO 12
<211> LENGTH: 35
<212> TYPE: DNA
<213> ORGANISM: Artificial Sequence
<220> FEATURE:
<223> OTHER INFORMATION: primer

<400> SEQUENCE: 12
```
caggtcgact ctagacgcta aatttagcgc tcctc        35

<210> SEQ ID NO 13
<211> LENGTH: 30
<212> TYPE: DNA
<213> ORGANISM: Artificial Sequence
<220> FEATURE:
<223> OTHER INFORMATION: primer

<400> SEQUENCE: 13
ggaggtggag catgcctgct cgtggtcagc        30

<210> SEQ ID NO 14
<211> LENGTH: 30
<212> TYPE: DNA
<213> ORGANISM: Artificial Sequence
<220> FEATURE:
<223> OTHER INFORMATION: primer

<400> SEQUENCE: 14
gaccacgagc aggcatgctc cacctccacc        30

<210> SEQ ID NO 15
<211> LENGTH: 30
<212> TYPE: DNA
<213> ORGANISM: Artificial Sequence
<220> FEATURE:
<223> OTHER INFORMATION: primer

<400> SEQUENCE: 15
ggaggtggag cagacctgct cgtggtcagc        30

<210> SEQ ID NO 16
<211> LENGTH: 30
<212> TYPE: DNA
<213> ORGANISM: Artificial Sequence
<220> FEATURE:
<223> OTHER INFORMATION: primer

<400> SEQUENCE: 16
gaccacgagc aggtctgctc cacctccacc        30

<210> SEQ ID NO 17
<211> LENGTH: 30
<212> TYPE: DNA
<213> ORGANISM: Artificial Sequence
<220> FEATURE:
<223> OTHER INFORMATION: primer

<400> SEQUENCE: 17
ggaggtggag cactgctgct cgtggtcagc        30

<210> SEQ ID NO 18
<211> LENGTH: 30
<212> TYPE: DNA
<213> ORGANISM: Artificial Sequence
<220> FEATURE:
<223> OTHER INFORMATION: primer

<400> SEQUENCE: 18
gaccacgagc agcagtgctc cacctccacc        30

<210> SEQ ID NO 19
<211> LENGTH: 30
<212> TYPE: DNA

```
<213> ORGANISM: Artificial Sequence
<220> FEATURE:
<223> OTHER INFORMATION: primer

<400> SEQUENCE: 19
ggaggtggag cagtgctgct cgtggtcagc                                    30

<210> SEQ ID NO 20
<211> LENGTH: 30
<212> TYPE: DNA
<213> ORGANISM: Artificial Sequence
<220> FEATURE:
<223> OTHER INFORMATION: primer

<400> SEQUENCE: 20
gaccacgagc agcactgctc cacctccacc                                    30

<210> SEQ ID NO 21
<211> LENGTH: 30
<212> TYPE: DNA
<213> ORGANISM: Artificial Sequence
<220> FEATURE:
<223> OTHER INFORMATION: primer

<400> SEQUENCE: 21
ggaggtggag cagcgctgct cgtggtcagc                                    30

<210> SEQ ID NO 22
<211> LENGTH: 30
<212> TYPE: DNA
<213> ORGANISM: Artificial Sequence
<220> FEATURE:
<223> OTHER INFORMATION: primer

<400> SEQUENCE: 22
gaccacgagc agcgctgctc cacctccacc                                    30

<210> SEQ ID NO 23
<211> LENGTH: 30
<212> TYPE: DNA
<213> ORGANISM: Artificial Sequence
<220> FEATURE:
<223> OTHER INFORMATION: primer

<400> SEQUENCE: 23
ggaggtggag catggctgct cgtggtcagc                                    30

<210> SEQ ID NO 24
<211> LENGTH: 30
<212> TYPE: DNA
<213> ORGANISM: Artificial Sequence
<220> FEATURE:
<223> OTHER INFORMATION: primer

<400> SEQUENCE: 24
gaccacgagc agccatgctc cacctccacc                                    30

<210> SEQ ID NO 25
<211> LENGTH: 30
<212> TYPE: DNA
<213> ORGANISM: Artificial Sequence
<220> FEATURE:
<223> OTHER INFORMATION: primer

<400> SEQUENCE: 25
ggaggtggag cacagctgct cgtggtcagc                                    30
```

<210> SEQ ID NO 26
<211> LENGTH: 30
<212> TYPE: DNA
<213> ORGANISM: Artificial Sequence
<220> FEATURE:
<223> OTHER INFORMATION: primer

<400> SEQUENCE: 26
gaccacgagc agctgtgctc cacctccacc                                    30

<210> SEQ ID NO 27
<211> LENGTH: 30
<212> TYPE: DNA
<213> ORGANISM: Artificial Sequence
<220> FEATURE:
<223> OTHER INFORMATION: primer

<400> SEQUENCE: 27
ggaggtggag cagtactgct cgtggtcagc                                    30

<210> SEQ ID NO 28
<211> LENGTH: 30
<212> TYPE: DNA
<213> ORGANISM: Artificial Sequence
<220> FEATURE:
<223> OTHER INFORMATION: primer

<400> SEQUENCE: 28
gaccacgagc agtactgctc cacctccacc                                    30

<210> SEQ ID NO 29
<211> LENGTH: 30
<212> TYPE: DNA
<213> ORGANISM: Artificial Sequence
<220> FEATURE:
<223> OTHER INFORMATION: primer

<400> SEQUENCE: 29
ggaggtggag caggactgct cgtggtcagc                                    30

<210> SEQ ID NO 30
<211> LENGTH: 30
<212> TYPE: DNA
<213> ORGANISM: Artificial Sequence
<220> FEATURE:
<223> OTHER INFORMATION: primer

<400> SEQUENCE: 30
gaccacgagc agtcctgctc cacctccacc                                    30

<210> SEQ ID NO 31
<211> LENGTH: 30
<212> TYPE: DNA
<213> ORGANISM: Artificial Sequence
<220> FEATURE:
<223> OTHER INFORMATION: primer

<400> SEQUENCE: 31
ggaggtggag cacttctgct cgtggtcagc                                    30

<210> SEQ ID NO 32
<211> LENGTH: 30
<212> TYPE: DNA
<213> ORGANISM: Artificial Sequence
<220> FEATURE:

<223> OTHER INFORMATION: primer

<400> SEQUENCE: 32
gaccacgagc agaagtgctc cacctccacc                                          30

<210> SEQ ID NO 33
<211> LENGTH: 30
<212> TYPE: DNA
<213> ORGANISM: Artificial Sequence
<220> FEATURE:
<223> OTHER INFORMATION: primer

<400> SEQUENCE: 33
ggaggtggag cacatctgct cgtggtcagc                                          30

<210> SEQ ID NO 34
<211> LENGTH: 30
<212> TYPE: DNA
<213> ORGANISM: Artificial Sequence
<220> FEATURE:
<223> OTHER INFORMATION: primer

<400> SEQUENCE: 34
gaccacgagc agatgtgctc cacctccacc                                          30

<210> SEQ ID NO 35
<211> LENGTH: 30
<212> TYPE: DNA
<213> ORGANISM: Artificial Sequence
<220> FEATURE:
<223> OTHER INFORMATION: primer

<400> SEQUENCE: 35
ggaggtggag cagatctgct cgtggtcagc                                          30

<210> SEQ ID NO 36
<211> LENGTH: 30
<212> TYPE: DNA
<213> ORGANISM: Artificial Sequence
<220> FEATURE:
<223> OTHER INFORMATION: primer

<400> SEQUENCE: 36
gaccacgagc agatctgctc cacctccacc                                          30

<210> SEQ ID NO 37
<211> LENGTH: 30
<212> TYPE: DNA
<213> ORGANISM: Artificial Sequence
<220> FEATURE:
<223> OTHER INFORMATION: primer

<400> SEQUENCE: 37
ggaggtggag cattcctgct cgtggtcagc                                          30

<210> SEQ ID NO 38
<211> LENGTH: 30
<212> TYPE: DNA
<213> ORGANISM: Artificial Sequence
<220> FEATURE:
<223> OTHER INFORMATION: primer

<400> SEQUENCE: 38
gaccacgagc aggaatgctc cacctccacc                                          30

```
<210> SEQ ID NO 39
<211> LENGTH: 30
<212> TYPE: DNA
<213> ORGANISM: Artificial Sequence
<220> FEATURE:
<223> OTHER INFORMATION: primer

<400> SEQUENCE: 39
ggaggtggag cagtcctgct cgtggtcagc                                    30

<210> SEQ ID NO 40
<211> LENGTH: 30
<212> TYPE: DNA
<213> ORGANISM: Artificial Sequence
<220> FEATURE:
<223> OTHER INFORMATION: primer

<400> SEQUENCE: 40
gaccacgagc aggactgctc cacctccacc                                    30

<210> SEQ ID NO 41
<211> LENGTH: 30
<212> TYPE: DNA
<213> ORGANISM: Artificial Sequence
<220> FEATURE:
<223> OTHER INFORMATION: primer

<400> SEQUENCE: 41
ggaggtggag cagccctgct cgtggtcagc                                    30

<210> SEQ ID NO 42
<211> LENGTH: 30
<212> TYPE: DNA
<213> ORGANISM: Artificial Sequence
<220> FEATURE:
<223> OTHER INFORMATION: primer

<400> SEQUENCE: 42
gaccacgagc agggctgctc cacctccacc                                    30

<210> SEQ ID NO 43
<211> LENGTH: 30
<212> TYPE: DNA
<213> ORGANISM: Artificial Sequence
<220> FEATURE:
<223> OTHER INFORMATION: primer

<400> SEQUENCE: 43
ggaggtggag cagcactgct cgtggtcagc                                    30

<210> SEQ ID NO 44
<211> LENGTH: 30
<212> TYPE: DNA
<213> ORGANISM: Artificial Sequence
<220> FEATURE:
<223> OTHER INFORMATION: primer

<400> SEQUENCE: 44
gaccacgagc agtggtgctc cacctccacc                                    30

<210> SEQ ID NO 45
<211> LENGTH: 30
<212> TYPE: DNA
<213> ORGANISM: Artificial Sequence
<220> FEATURE:
<223> OTHER INFORMATION: primer
```

```
<400> SEQUENCE: 45
ggaggtggag cagcactgct cgtggtcagc                              30

<210> SEQ ID NO 46
<211> LENGTH: 30
<212> TYPE: DNA
<213> ORGANISM: Artificial Sequence
<220> FEATURE:
<223> OTHER INFORMATION: primer

<400> SEQUENCE: 46
gaccacgagc agtgctgctc cacctccacc                              30

<210> SEQ ID NO 47
<211> LENGTH: 30
<212> TYPE: DNA
<213> ORGANISM: Artificial Sequence
<220> FEATURE:
<223> OTHER INFORMATION: primer

<400> SEQUENCE: 47
ggaggtggag cagaactgct cgtggtcagc                              30

<210> SEQ ID NO 48
<211> LENGTH: 30
<212> TYPE: DNA
<213> ORGANISM: Artificial Sequence
<220> FEATURE:
<223> OTHER INFORMATION: primer

<400> SEQUENCE: 48
gaccacgagc agttctgctc cacctccacc                              30

<210> SEQ ID NO 49
<211> LENGTH: 30
<212> TYPE: DNA
<213> ORGANISM: Artificial Sequence
<220> FEATURE:
<223> OTHER INFORMATION: primer

<400> SEQUENCE: 49
ggaggtggag caggtctgct cgtggtcagc                              30

<210> SEQ ID NO 50
<211> LENGTH: 30
<212> TYPE: DNA
<213> ORGANISM: Artificial Sequence
<220> FEATURE:
<223> OTHER INFORMATION: primer

<400> SEQUENCE: 50
gaccacgagc agacctgctc cacctccacc                              30

<210> SEQ ID NO 51
<211> LENGTH: 29
<212> TYPE: DNA
<213> ORGANISM: Artificial Sequence
<220> FEATURE:
<223> OTHER INFORMATION: primer

<400> SEQUENCE: 51
tcctctagac tggtcgcctg atgttctac                               29

<210> SEQ ID NO 52
<211> LENGTH: 29
```

```
<212> TYPE: DNA
<213> ORGANISM: Artificial Sequence
<220> FEATURE:
<223> OTHER INFORMATION: primer

<400> SEQUENCE: 52
gactctagat tagtcccttt cgaggcgga                                29

<210> SEQ ID NO 53
<211> LENGTH: 20
<212> TYPE: DNA
<213> ORGANISM: Artificial Sequence
<220> FEATURE:
<223> OTHER INFORMATION: primer

<400> SEQUENCE: 53
gccaaaacct ccacgcgatc                                          20

<210> SEQ ID NO 54
<211> LENGTH: 20
<212> TYPE: DNA
<213> ORGANISM: Artificial Sequence
<220> FEATURE:
<223> OTHER INFORMATION: primer

<400> SEQUENCE: 54
atcgcgtgga ggttttggct                                          20

<210> SEQ ID NO 55
<211> LENGTH: 28
<212> TYPE: DNA
<213> ORGANISM: Artificial Sequence
<220> FEATURE:
<223> OTHER INFORMATION: primer

<400> SEQUENCE: 55
acggatccca gactccaaag caaaagcg                                 28

<210> SEQ ID NO 56
<211> LENGTH: 28
<212> TYPE: DNA
<213> ORGANISM: Artificial Sequence
<220> FEATURE:
<223> OTHER INFORMATION: primer

<400> SEQUENCE: 56
acggatccaa ccaaacttgc tcacactc                                 28

<210> SEQ ID NO 57
<211> LENGTH: 30
<212> TYPE: DNA
<213> ORGANISM: Artificial Sequence
<220> FEATURE:
<223> OTHER INFORMATION: primer

<400> SEQUENCE: 57
acaccacggc agaaccaggt gcaaaggaca                               30

<210> SEQ ID NO 58
<211> LENGTH: 30
<212> TYPE: DNA
<213> ORGANISM: Artificial Sequence
<220> FEATURE:
<223> OTHER INFORMATION: primer

<400> SEQUENCE: 58
```
ctggttctgc cgtggtgtgc atcatctctg 30

<210> SEQ ID NO 59
<211> LENGTH: 437
<212> TYPE: PRT
<213> ORGANISM: Unknown
<220> FEATURE:
<223> OTHER INFORMATION: N241S

<400> SEQUENCE: 59

Met Phe Glu Arg Asp Ile Val Ala Thr Asp Asn Asn Lys Ala Val Leu
1               5                   10                  15

His Tyr Pro Gly Gly Glu Phe Glu Met Asp Ile Ile Glu Ala Ser Glu
            20                  25                  30

Gly Asn Asn Gly Val Val Leu Gly Lys Met Leu Ser Glu Thr Gly Leu
        35                  40                  45

Ile Thr Phe Asp Pro Gly Tyr Val Ser Thr Gly Ser Thr Glu Ser Lys
    50                  55                  60

Ile Thr Tyr Ile Asp Gly Asp Ala Gly Ile Leu Arg Tyr Arg Gly Tyr
65                  70                  75                  80

Asp Ile Ala Asp Leu Ala Glu Asn Ala Thr Phe Asn Glu Val Ser Tyr
                85                  90                  95

Leu Leu Ile Asn Gly Glu Leu Pro Thr Pro Asp Glu Leu His Lys Phe
            100                 105                 110

Asn Asp Glu Ile Arg His His Thr Leu Leu Asp Glu Asp Phe Lys Ser
        115                 120                 125

Gln Phe Asn Val Phe Pro Arg Asp Ala His Pro Met Ala Thr Leu Ala
    130                 135                 140

Ser Ser Val Asn Ile Leu Ser Thr Tyr Tyr Gln Asp Gln Leu Asn Pro
145                 150                 155                 160

Leu Asp Glu Ala Gln Leu Asp Lys Ala Thr Val Arg Leu Met Ala Lys
                165                 170                 175

Val Pro Met Leu Ala Ala Tyr Ala His Arg Ala Arg Lys Gly Ala Pro
            180                 185                 190

Tyr Met Tyr Pro Asp Asn Ser Leu Asn Ala Arg Glu Asn Phe Leu Arg
        195                 200                 205

Met Met Phe Gly Tyr Pro Thr Glu Pro Tyr Glu Ile Asp Pro Ile Met
    210                 215                 220

Val Lys Ala Leu Asp Lys Leu Leu Ile Leu His Ala Asp His Glu Gln
225                 230                 235                 240

Ser Cys Ser Thr Ser Thr Val Arg Met Ile Gly Ser Ala Gln Ala Asn
                245                 250                 255

Met Phe Val Ser Ile Ala Gly Gly Ile Asn Ala Leu Ser Gly Pro Leu
            260                 265                 270

His Gly Gly Ala Asn Gln Ala Val Leu Glu Met Leu Glu Asp Ile Lys
        275                 280                 285

Ser Asn His Gly Gly Asp Ala Thr Glu Phe Met Asn Lys Val Lys Asn
    290                 295                 300

Lys Glu Asp Gly Val Arg Leu Met Gly Phe Gly His Arg Val Tyr Lys
305                 310                 315                 320

Asn Tyr Asp Pro Arg Ala Ala Ile Val Lys Glu Thr Ala His Glu Ile
                325                 330                 335

Leu Glu His Leu Gly Gly Asp Asp Leu Leu Asp Leu Ala Ile Lys Leu
            340                 345                 350

Glu Glu Ile Ala Leu Ala Asp Asp Tyr Phe Ile Ser Arg Lys Leu Tyr

```
                355                 360                 365
Pro Asn Val Asp Phe Tyr Thr Gly Leu Ile Tyr Arg Ala Met Gly Phe
    370                 375                 380

Pro Thr Asp Phe Phe Thr Val Leu Phe Ala Ile Gly Arg Leu Pro Gly
385                 390                 395                 400

Trp Ile Ala His Tyr Arg Glu Gln Leu Gly Ala Ala Gly Asn Lys Ile
                405                 410                 415

Asn Arg Pro Arg Gln Val Tyr Thr Gly Asn Glu Ser Arg Lys Leu Val
            420                 425                 430

Pro Arg Glu Glu Arg
        435

<210> SEQ ID NO 60
<211> LENGTH: 1314
<212> TYPE: DNA
<213> ORGANISM: Unknown
<220> FEATURE:
<223> OTHER INFORMATION: N241S

<400> SEQUENCE: 60
atgtttgaaa gggatatcgt ggctactgat aacaacaagg ctgtcctgca ctaccccggt      60
ggcgagttcg aaatggacat catcgaggct tctgagggta caacggtgt tgtcctgggc      120 aagatgctgt ctgagactgg actgatcact tttgacccag ttatgtgag cactggctcc      180 accgagtcga agatcaccta catcgatggc gatgcgggaa tcctgcgtta ccgcggctat      240
gacatcgctg atctggctga gaatgccacc ttcaacgagg tttcttacct acttatcaac      300
ggtgagctac caaccccaga tgagcttcac aagtttaacg acgagattcg ccaccacacc      360
cttctggacg aggacttcaa gtcccagttc aacgtgttcc cacgcgacgc tcacccaatg      420
gcaaccttgg cttcctcggt taacattttg tctacctact accaggacca gctgaaccca      480
ctcgatgagg cacagcttga taaggcaacc gttcgcctca tggcaaaggt tccaatgctg      540
gctgcgtacg cacaccgcgc acgcaagggt gctccttaca tgtacccaga caactccctc      600
aatgcgcgtg agaacttcct gcgcatgatg ttcggttacc caaccgagcc atacgagatc      660
gacccaatca tggtcaaggc tctggacaag ctgctcatcc tgcacgctga ccacgagcag      720
tcctgctcca cctccaccgt tcgtatgatc ggttccgcac aggccaacat gtttgtctcc      780
atcgctggtg gcatcaacgc tctgtccggc ccactgcacg tggcgcaaaa ccaggctgtt      840
ctggagatgc tcgaagacat caagagcaac acggtggcg acgcaaccga gttcatgaac      900
aaggtcaaga caaggaaga cggcgtccgc ctcatgggct tcggacaccg cgtttacaag      960
aactacgatc cacgtgcagc aatcgtcaag gagaccgcac acgagatcct cgagcacctc      1020
ggtggcgacg atcttctgga tctggcaatc aagctggaag aaattgcact ggctgatgat      1080
tacttcatct cccgcaagct ctacccgaac gtagacttct acaccggcct gatctaccgc      1140
gcaatgggct tcccaactga cttcttcacc gtattgttcg caatcggtcg tctgccagga      1200
tggatcgctc actaccgcga gcagctcggt gcagcaggca caagatcaa ccgcccacgc      1260 caggtctaca ccggcaacga atcccgcaag ttggttcctc gcgaggagcg ctaa            1314

<210> SEQ ID NO 61
<211> LENGTH: 437
<212> TYPE: PRT
<213> ORGANISM: Unknown
<220> FEATURE:
<223> OTHER INFORMATION: N241Y
```

<400> SEQUENCE: 61

```
Met Phe Glu Arg Asp Ile Val Ala Thr Asp Asn Asn Lys Ala Val Leu
1               5                   10                  15

His Tyr Pro Gly Gly Glu Phe Glu Met Asp Ile Ile Glu Ala Ser Glu
            20                  25                  30

Gly Asn Asn Gly Val Val Leu Gly Lys Met Leu Ser Glu Thr Gly Leu
            35                  40                  45

Ile Thr Phe Asp Pro Gly Tyr Val Ser Thr Gly Ser Thr Glu Ser Lys
50                  55                  60

Ile Thr Tyr Ile Asp Gly Asp Ala Gly Ile Leu Arg Tyr Arg Gly Tyr
65                  70                  75                  80

Asp Ile Ala Asp Leu Ala Glu Asn Ala Thr Phe Asn Glu Val Ser Tyr
                85                  90                  95

Leu Leu Ile Asn Gly Glu Leu Pro Thr Pro Asp Glu Leu His Lys Phe
            100                 105                 110

Asn Asp Glu Ile Arg His His Thr Leu Leu Asp Glu Asp Phe Lys Ser
            115                 120                 125

Gln Phe Asn Val Phe Pro Arg Asp Ala His Pro Met Ala Thr Leu Ala
130                 135                 140

Ser Ser Val Asn Ile Leu Ser Thr Tyr Tyr Gln Asp Gln Leu Asn Pro
145                 150                 155                 160

Leu Asp Glu Ala Gln Leu Asp Lys Ala Thr Val Arg Leu Met Ala Lys
                165                 170                 175

Val Pro Met Leu Ala Ala Tyr Ala His Arg Ala Arg Lys Gly Ala Pro
            180                 185                 190

Tyr Met Tyr Pro Asp Asn Ser Leu Asn Ala Arg Glu Asn Phe Leu Arg
            195                 200                 205

Met Met Phe Gly Tyr Pro Thr Glu Pro Tyr Glu Ile Asp Pro Ile Met
210                 215                 220

Val Lys Ala Leu Asp Lys Leu Leu Ile Leu His Ala Asp His Glu Gln
225                 230                 235                 240

Tyr Cys Ser Thr Ser Thr Val Arg Met Ile Gly Ser Ala Gln Ala Asn
                245                 250                 255

Met Phe Val Ser Ile Ala Gly Gly Ile Asn Ala Leu Ser Gly Pro Leu
            260                 265                 270

His Gly Gly Ala Asn Gln Ala Val Leu Glu Met Leu Glu Asp Ile Lys
            275                 280                 285

Ser Asn His Gly Gly Asp Ala Thr Glu Phe Met Asn Lys Val Lys Asn
290                 295                 300

Lys Glu Asp Gly Val Arg Leu Met Gly Phe Gly His Arg Val Tyr Lys
305                 310                 315                 320

Asn Tyr Asp Pro Arg Ala Ala Ile Val Lys Glu Thr Ala His Glu Ile
                325                 330                 335

Leu Glu His Leu Gly Gly Asp Asp Leu Leu Asp Leu Ala Ile Lys Leu
            340                 345                 350

Glu Glu Ile Ala Leu Ala Asp Asp Tyr Phe Ile Ser Arg Lys Leu Tyr
            355                 360                 365

Pro Asn Val Asp Phe Tyr Thr Gly Leu Ile Tyr Arg Ala Met Gly Phe
370                 375                 380

Pro Thr Asp Phe Phe Thr Val Leu Phe Ala Ile Gly Arg Leu Pro Gly
385                 390                 395                 400

Trp Ile Ala His Tyr Arg Glu Gln Leu Gly Ala Ala Gly Asn Lys Ile
                405                 410                 415
```

Asn Arg Pro Arg Gln Val Tyr Thr Gly Asn Glu Ser Arg Lys Leu Val
            420                 425                 430

Pro Arg Glu Glu Arg
        435

<210> SEQ ID NO 62
<211> LENGTH: 1314
<212> TYPE: DNA
<213> ORGANISM: Unknown
<220> FEATURE:
<223> OTHER INFORMATION: N241Y

<400> SEQUENCE: 62

| | | | | | |
|---|---|---|---|---|---|
| atgtttgaaa | gggatatcgt | ggctactgat | aacaacaagg | ctgtcctgca | ctaccccggt | 60 |
| ggcgagttcg | aaatggacat | catcgaggct | tctgagggta | acaacggtgt | tgtcctgggc | 120 |
| aagatgctgt | ctgagactgg | actgatcact | tttgacccag | gttatgtgag | cactggctcc | 180 |
| accgagtcga | agatcaccta | catcgatggc | gatgcgggaa | tcctgcgtta | ccgcggctat | 240 |
| gacatcgctg | atctggctga | gaatgccacc | ttcaacgagg | tttcttacct | acttatcaac | 300 |
| ggtgagctac | caaccccaga | tgagcttcac | aagtttaacg | acgagattcg | ccaccacacc | 360 |
| cttctggacg | aggacttcaa | gtcccagttc | aacgtgttcc | cacgcgacgc | tcacccaatg | 420 |
| gcaaccttgg | cttcctcggt | taacattttg | tctacctact | accaggacca | gctgaaccca | 480 |
| ctcgatgagg | cacagcttga | taaggcaacc | gttcgcctca | tggcaaaggt | tccaatgctg | 540 |
| gctgcgtacg | cacaccgcgc | acgcaagggt | gctccttaca | tgtacccaga | caactccctc | 600 |
| aatgcgcgtg | agaacttcct | gcgcatgatg | ttcggttacc | caaccgagcc | atacgagatc | 660 |
| gacccaatca | tggtcaaggc | tctggacaag | ctgctcatcc | tgcacgctga | ccacgagcag | 720 |
| tactgctcca | cctccaccgt | tcgtatgatc | ggttccgcac | aggccaacat | gtttgtctcc | 780 |
| atcgctggtg | gcatcaacgc | tctgtccggc | ccactgcacg | gtggcgcaaa | ccaggctgtt | 840 |
| ctggagatgc | tcgaagacat | caagagcaac | cacggtggcg | acgcaaccga | gttcatgaac | 900 |
| aaggtcaaga | acaaggaaga | cggcgtccgc | ctcatgggct | tcggacaccg | cgtttacaag | 960 |
| aactacgatc | cacgtgcagc | aatcgtcaag | gagaccgcac | acgagatcct | cgagcacctc | 1020 |
| ggtggcgacg | atcttctgga | tctggcaatc | aagctggaag | aaattgcact | ggctgatgat | 1080 |
| tacttcatct | cccgcaagct | ctacccgaac | gtagacttct | acaccggcct | gatctaccgc | 1140 |
| gcaatgggct | tcccaactga | cttcttcacc | gtattgttcg | caatcggtcg | tctgccagga | 1200 |
| tggatcgctc | actaccgcga | gcagctcggt | gcagcaggca | acaagatcaa | ccgcccacgc | 1260 |
| caggtctaca | ccggcaacga | atcccgcaag | ttggttcctc | gcgaggagcg | ctaa | 1314 |